(12) United States Patent
Cahoon et al.

(10) Patent No.: US 6,670,166 B1
(45) Date of Patent: Dec. 30, 2003

(54) ARTHROPOD PROTEIN DISULFIDE ISOMERASES

(75) Inventors: Rebecca E. Cahoon, Wilmington, DE (US); Rafael Herrmann, Wilmington, DE (US); Albert L. Lu, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/807,258

(22) PCT Filed: Oct. 14, 1999

(86) PCT No.: PCT/US99/23813
§ 371 (c)(1),
(2), (4) Date: Apr. 9, 2001

(87) PCT Pub. No.: WO00/22100
PCT Pub. Date: Apr. 20, 2000

Related U.S. Application Data

(60) Provisional application No. 60/104,376, filed on Oct. 15, 1998.

(51) Int. Cl.$^7$ .......................... C12N 9/90; C12N 15/61; C12N 15/74; C12N 15/80; C12N 15/82

(52) U.S. Cl. ................. 435/233; 435/320.1; 435/235.1; 435/410; 435/252.3; 536/23.2

(58) Field of Search .............................. 435/233, 320.1, 435/235.1, 410, 252.3; 536/23.2

(56) References Cited

FOREIGN PATENT DOCUMENTS

| EP | 0 509 841 A2 | 10/1992 |
|----|----|----|
| WO | 98/06835 | 2/1998 |

OTHER PUBLICATIONS

Vuori, K., et al. (1992) J. Biol. Chem. 267(11), 7211–7214.*
Richard R. McKay et al., Insect Biochem. Molec. Biol., vol. 25(5):647–654, 1995, A Drosophila Gene that Encodes a Member of the Protein Disulfide Isomerase/Phospholipase C–alpha Family.
Tsu–An Hsu et al., Protein Exp. & Purfification, vol. 7:281–288, 1996, Rescue of Immunoglobulins from Insolubility is Facilitated by PDI in the Baculovirus Expression System.
Richard A. Mazzarella et al., Journ. of Biol. Chem., vol. 265(2):1094–1101, 1990, ERp72, an Abundant Luminal Endoplasmic Reticulum Protein, Contains Three Copies of the Active Site Sequences of Protein Disulfide isomerase.
Peppi Koivunen et al., Biochem. J., vol. 316:599–605, 1996, ERp60 does not substitute for protein disulphide isomerase as the beta–subunit of prolyl 4–hydroxylase.
Peppi Koivunen et al., Genomics, 42:397–404, 1997, Structures of the Human Gene for the Protein Disulfide isomerase–Related Polypeptide ERp60 and a Processed Gene and Assignment of These Genes to 15q15 and 1q21.

Basil S. Shorrosh et al., The Plant J., vol. 2(1):51–58, 1992, Molecular characterization and expression of an alfalfa protein with sequence similarity to mammalian ERp72, a glucose–regulated endoplasmic reticulum protein containing active site sequences of protein disulphide isomerase.
Muraru M. Chaudhuri et al., Biochem. J., 281:645–650, 1992, The gene for a novel protein, a member of the protein disulphide isomerase/Form I phosphoinositide–specific phospholipase C family, is amplified in hydroxyurea–resistant cells.
Jie–Min Wong et al., Gene, 150:175–179, 1994, Cloning of a cDNA encoding an *Acanthamoeba castellanii* PDI–like protein.
National Center for Biotechnology Information General Identifier No. 4262594, Feb. 11, 1999, Wilson, R. et al., 2.2 Mb of contiguous nucleotide sequence from chromosome III of *C. elegans*.
R. Wilson et al., Nature, 368:32–38, 1994, 2.2 Mb of contiguous nucleotide sequence from chromosome III of *C. elegans*.
National Center for Biotechnology Information General Identifier No. 1709616, Oct. 1, 2000, McKay, R. R. et al., A Drosophila gene that encodes a member of the protein disulfide isomerase/phospholipasse C–alpha family.
Mark D. Adams et al., Science, 287:2185–2195, 2000, The Genome Sequence of *Drosophila melanogaster*.
National Center for Biotechnology Information General Identifier No. 2144546, May 19, 2000, Nakazawa, M. et al., Structure of the gene encoding the beta–subunit of chicken prolyl 4–hydroxylase.
Mitsuru Nakazawa et al., Gene, 71:451–460, 1988, Structure of the gene encoding the beta–subunit of chicken prolyl 4–hydroxylase.
Tarja Parkkonen et al., Biochem. J., 256:1005–1011, 1988, Molecular cloning of a multifunctional chicken protein acting as the prolyl 4–hydroxylase beta–subunit, protein disulphide–isomerase and a cellular thyroid–hormone–binding protein.
National Center for Biotechnology Information General Identifier No. 1699220, Dec. 3, 1996, Koivunen, P. et al., ERp60 does not substitute for protein disulphide isomerase as the beta–subunit of prolyl 4–hydroxylase.
National Center for Biotechnology Information General Identifier No. 2507460, Oct. 1, 2000, Pihlajaniemi, T. et al., Molecular cloning of the beta–subunit of human prolyl 4–hydroxylase. This subunit and protein disulphide isomerase are products of the same gene.

(List continued on next page.)

Primary Examiner—Charles L. Patterson, Jr.

(57) ABSTRACT

This invention relates to an isolated nucleic acid fragment encoding protein disulfide isomerase. The invention also relates to the construction of a chimeric gene encoding all or a portion of the protein disulfide isomerase, in sense or antisense orientation, wherein expression of the chimeric gene results in production of altered levels of the protein disulfide isomerase in a transformed host cell.

16 Claims, 11 Drawing Sheets

OTHER PUBLICATIONS

Johan Kemmink et al., J. of Biomolecular NMR, 13:357–368, 1999, The structure in solution of the beta domain of protein disulfide isomerase.

Johan Kemmink et al., Biochemistry, 35:7684–7691, 1996, Structure determination of the N–Terminal Thioredoxin–like Domain of Protein Disulfide Isomerase Using Multidimensional Heteronuclear 13C/15N NMR Spectroscopy.

Johan Kemmink et al., Protein Science, 4:2587–2593, 1995, Nuclear magnetic resonance charcterization of the N–terminal thioredoxin–like domain of protein disulfide isomerase.

Hong Ji et al., Electrophoresis, 18:605–613, 1997, A two–dimensional gel database of human colon carcinoma proteins.

Denis F. Hochstrasser et al., Electrophoresis, 13:992–1001, 1992, Human liver protein map: A reference database established by microsequencing and gel comparison.

Jonathan I. Morris et al., Biochimica et Biophysica Acta, 949:169–180, 1988, Characterization of a cDNA for human glutathione–insulin transhydrogenase (protein–disulfide isomerase/oxidoreductase).

Sheue–Yann Cheng et al., Journ. of Biol. Chem., 262(23):11221–11227, 1987, The nucleotide sequence of a human cellular thyroid hormone binding protein present in endoplasmic reticulum.

Taina Pihlajaniemi et al., EMBO J., 6(3):643–649, 1987, Molecular cloning of the beta–subunit of human prolyl 4–hydroxylase. The subunit and protein disulphide isomerase are products of the same gene.

National Center for Biotechnology Information General Identifier No. 729442, Feb. 1, 1995, Shorrosh, B. S. et al., Molecular characterization and expression of an alfalfa protein with sequence similariity to mammalian ERp72, a glucose–regulated endoplasmic reticulum protein containing active site sequences of protein disulphide isomerase.

National Center for Biotechnology Information General Identifier No. 2501206, Oct. 1, 2000, Fuellekrug, J. et al., CaBP1, a calcium binding protein of the thioredoxin family, is a resident KDEL protein of the ER and not of the intermediate compartment.

Joachim Fullekrug et al., J. of Cell Science, 107:2719–2727, 1994, CaBP1, a calcium binding protein of the thioredoxin family, is a resident KDEL protein of the ER and not of the intermediate compartment.

* cited by examiner

Figure 1A

```
              *                                             ****          ****       *            *******************
SEQ ID NO:27  MKFLIC-ALFLAASYVAA-SAEAEVKVEEGVLVATVDNFKQLIADNEFVLVEFYAPWCGH
SEQ ID NO:28  MAVVRVRAIVALLCLVAALGLAEPLEEEDGVLVRAANFEQALAAHRLLVEFYAPWCGH
SEQ ID NO:02  M-FIKL--LITTLC-IAS-TIADEIKKENHVLVLTNDNFEGAIKD-KNVLVEFYAPWCGH
SEQ ID NO:04  M-YIKL--LILSLC-IYL-CIADEIKKEKSVLVLTKDNFEGAIKD-KSVLVEFYAPWCGH
SEQ ID NO:06  MRVI----LFTALALLGT-ALADEVPTEENVLVLSKSNFEGVISANNFILVEFYAPWCGH
SEQ ID NO:08  M-LGAV-TLSTILL-VVI-AAADEIKKDGEVLVLNKDNFQKAIQENKHILVEFYAPWCGH
              1                                                          60

*  *  ******* *****        *    *  **     *   ***  **   *
SEQ ID NO:27  CKALAPEYAKAAQQLAEKESPIKLAKVDATVEGELAEQYAVRGYPTLKFFRSGS---PVE
SEQ ID NO:28  CKALAPEYAKAAAQLKAEGSEIRLAKVDATEEAELAQQFGVRGYPTIKFFRNGDKAAPRE
SEQ ID NO:02  CKALEPQYAKAAESLAEEKSELLLAKVDATVETDLAERYGVRGYPTIKFFREGK---IFE
SEQ ID NO:04  CKALEPEYAKAAQILEEEKSDLLLAKVDATAETDLAEQHGVRGYPTIKFFREGK---VIE
SEQ ID NO:06  CKSLAPEYAKAATKLAEEESPIKLAKVDATQEQELAESYGVRGYPTLKFFRNGS---PID
SEQ ID NO:08  CKALEPEYAKAAKQLKEEQSDIALGKIDATAESELAEEYDVRGYPTIKFIRDGK---PSE
              61                                                         120

*  *   ***** ****  ***     *  *          *   **  ****    *
SEQ ID NO:27  YSGGRQAADIIAWTKKTGPPAKDLTSVADAEQFLKDNEIAIIGFFKDLESEEAKTFTKV
SEQ ID NO:28  YTAGREADDIVSWLKKRTGPAATTLTDAAAAETLVDSSEVVIGFFKDVTSDAAKEFLLA
SEQ ID NO:02  YNGGRTSDEIIRWLKKKTGPPAVDLSSVEDAKKFVDSNEVAVVGFFKDLESADAKIFKSV
SEQ ID NO:04  YSGGRTADDIIRWLKKKTGPPATDLTTVEATKSFIDGGEVVVGFFKDQNSDQAKIFKNV
SEQ ID NO:06  YTGGRQADDIVSWLKKKTGPP------------------------------------
SEQ ID NO:08  YKGGRTAEDIVRWLKKKVGPPAENLDTVDSVKTFQSSAEVVLVGFFKDQSSDKAKVFLEV
              121                                                        180
```

Figure 1B

```
              *  + ** ****  *** **** *******     *** ****** *** ** *      ****
SEQ ID NO:27  ANALDSFVFGVSSNADVIAKYEAKDNGVVLFKPFDDKKSVFEGELNEENLKKFAQVQSLP
SEQ ID NO:28  AESVDDIPFGISSSADVFSKYQLSQDGVVLFKKFDEGRNNFEGDLTKDNLLNFIKSNQLP
SEQ ID NO:02  ASEMDDFVFGITDDDVVYSELKASKDGVILFKKFDEGRNEYEGELKEEDLKKFLKSNSLP
SEQ ID NO:04  AAEMDDFVFGITSTDEVYNELKATQDGVVLFKKFDEGRNVYEGELSEEKLKKFLKSNSLP
SEQ ID NO:06  ------------------------------------------------------------
SEQ ID NO:08  ALESDDYAFGITSQDDVFKAYNVEKDGIVLFKQFDEGRNDFEGEITADALKEFINANSLP
                                                                       240
                                                                       181

******     *+* ***   *+*+*+***** **        *         *        *        ** *+++++ **  ** *  +
SEQ ID NO:27  LIVDFNHESASKIFGGSIKSHLLFFVSRE-GGHIEKYVDPLKEIAKKYRDDILFVTISSD
SEQ ID NO:28  LVIEFTEQTAPKIFGGEIKTHILLFLPKS-VSDYEGKLDNFKTAAGNFKGKILFIFIDSD
SEQ ID NO:02  LVVEFSHETAQKIFGGDIKAHNLLFISKE-SSDYESRVDVFRKVAKEFKGKVLFVTINTD
SEQ ID NO:04  LVVEFTHESAQKIFGGDIKAHNLLFISKG-TSDYESKIEAFRKVAKEFKGKVLFVTIDTD
SEQ ID NO:06  ------------------------------------------------------------
SEQ ID NO:08  LVVEFNQDTAQKVFGGEIKAHNLLFVSKQQSEEYEKLLEVFRKVAKDFKNKVLFVTIDID
                                                                       300
                                                                       241

***+  *+ *** ****    ** *   *    *       *   **+*    *     *  *  + *  *+ ++*  ****
SEQ ID NO:27  EEDHTRIFEFFGMNKEEVPTIRLIKLEEDMAKYKPESDDLSAETIEAFLKKFLDGKLKQH
SEQ ID NO:28  HSDNQRILEFFGLKKECPAVRLITLEEEMTKYKPESDDLTADKIKEFCNKFLEGKIKPH
SEQ ID NO:02  DEDHEKIMDFFGLKKEDTPTMRLIKLEEEMAKFKPPTEGNSESEIRDFVNGVLEGKIKQH
SEQ ID NO:04  DEDHERIMEFFGLKKEEAPTMRLIKLEDEMTKFKPTTGIEESDIRGFVTGVLEGKIKQH
SEQ ID NO:06  ------------------------------------------------------------
SEQ ID NO:08  EEDHERIMEFFGMKKEDAPDMRLIRLEEEMTKFKPPSPGLSEENIRSFVQGVLDGKIKRH
                                                                       360
                                                                       301
```

Figure 1C

```
              **** *  **** ***  *** *** +  * ********** ****************  +*****
SEQ ID NO:27  LLSQELPEDWDKNPVKVLVSSNFESVALDKSKSVLVEFYAPWCGHCKQLAPIYDQLAEKY
SEQ ID NO:28  LMSQDLPEDWDKQPVKVLVGKNFEEVAFDENKNVFVEFYAPWCGHCKQLAPIWDKLGETY
SEQ ID NO:02  LLSEDIPEGWDKEPVKVLVGKNFDEVAFDKSKNVLVEFYAPWCGHCKQLAPIYDELGEKY
SEQ ID NO:04  LLSEDVPEGWDKEPVKILVGKNFDEVVFDKTKNVLVEFYAPWCGHCKQLAPIYDELGEKY
SEQ ID NO:06  ------------------------------------------------------------
SEQ ID NO:08  LLSESVPDDWDKGAVKVLVGQNFDDVAFDKSKDVLVEFYAPWCGHCKQLAPIYEELGEKY
              361                                                        420

**  **********+ ****  * ****  *   *   * ** ** *  ******    *
SEQ ID NO:27  KDNEDIVIAKMDSTANELESIKISSFPTIKYFRKEDN-KVIDFNLDRTLDDFVKFLDANG
SEQ ID NO:28  RDHENIVIAKMDSTANEVEAVKIHSFPTLKFFPAGSGRNVIDYNGERTLEGFKKFLESGG
SEQ ID NO:02  KDRDDVVIAKMDATANELEHTKINSYPTIKLYKKGTN-EVVEYNGERTLEGINKFTETDG
SEQ ID NO:04  KDQADIVIAKMDATANELEHTKINSFPTIKLYKKDTN-EVVDFNGERTLEGISRFIDTGG
SEQ ID NO:06  ------------------------------------------------------------
SEQ ID NO:08  KDQSSIVIAKMDATTNELDHVKIHSFPTIKLFKKDTN-EVIDFNGERTLEGLTKFIDSGG
              421                                                        480

*              **           +         + +***
SEQ ID NO:27  E----VADSEPV-------EETEEEEEAPKKDEL
SEQ ID NO:28  QDGAAADDDLEDLETDEETDLEEGDDDEQKIQKDEL
SEQ ID NO:02  EYGKAAPDEEEA-------EEAVREDAQAHRDEL
SEQ ID NO:04  VDGAAVKEEEED-------EEEEKDDEQAKRDEL
SEQ ID NO:06  ------------------------------------
SEQ ID NO:08  VDGASPKEEEID-------EEEEKDDDEKKRDEL
              481                              516
```

Figure 2A

```
                   *                                                          **
SEQ ID NO:29       MMWRLAGVLLLGFIA--ISSGADEDVLELGDDFATTLKQHETTLVMFYAPWCGHCKRLK
SEQ ID NO:10       M--KL--LFLSSILSCTLSVILCSDVLDFSGADFEDRIAEHDAILVEFFAPWCGHCKRLA
SEQ ID NO:12       ------------------------------------------------------TRLG
SEQ ID NO:14       M-WKI--V----AFSCFFVATIASDVLEFTDSDFDERIKEHDTYLVEFYAPWCGHCKRLA
                   1                                                          60

*  *  * +*+*  *** **** * ** *** *  +******* +*****  + +* *
SEQ ID NO:29       PEYAKAAEIVKDDDPPIKLAKVDCT-EAGKETCSKYSVSGYPTLKIFRQDEVSQDYNGPR
SEQ ID NO:10       PEYDKASTILKKADPPIPLAKVDCTSDNGKDTCSKYGVSGYPTLKIFRGGEFSSEYNGPR
SEQ ID NO:12       PKYEEAATILKKNDPPVPLAKVDCTSDAGKETCSKYGVSGYPTLKIFRNGEFSSEYSGGR
SEQ ID NO:14       PEYEKAATILKDNDPPIPLVKVDCI-ESGKETCGKFGVSGYPTLKIFRNDFSQEYNGPR
                   61                                                         120

*+***  ***** +                    +            *+ * *** *
SEQ ID NO:29       DSSGIAKYMRAQVGPASKTVRTVAELKKFLDTKDTTLFGYFSDSDSKLAKIFLKFADKNR
SEQ ID NO:10       DADGIVKYMKAQVGPSSKELQSLEDAEKIL-KDDIVIGYFADSNKLKEEFLKAADKLR
SEQ ID NO:12       ETDAIVKYMKSQVGPSSVEIKTPADAKKLLSRIEVVIIGFFKDEKSQLKEEFLKVADKMR
SEQ ID NO:14       EANGIVKYMAAQVGPSSKEFQNVKEVQQFLEKEEVAIIGFFESEDAKLKATFQKVADKLR
                   121                                                        180

*   ****       *    +     +   ****       *+        *      +
SEQ ID NO:29       EKYRFGHSSEKEVLDKQGETDKIVLIRAPHLSNKFESSSIKFEG--SSESDLSTFVKENF
SEQ ID NO:10       ESVSFAHTSSKDILDKYGYSDEIVLYRPKIFWSKFEPQEIKYTGD-ADKGEISQFIKDNY
SEQ ID NO:12       ETTSFGHTSNQEVLDLYGYKDQIVLFRPQHLQSKFEEKELKYEGG-AEKSKIEDFIRENY
SEQ ID NO:14       ETARFGHSNSLVLKEYGYTNQVLFRPKHLQSKFEDSQVVYDGDKSDKQELEEFVNKNY
                   181                                                        240
```

Figure 2B

```
                 ********** ** *  * ** ********** **********  ****   *** ++
SEQ ID NO:29     HGLVGHRTQDSVKDFQNPLITAYYSSVDYYQKNPKGTNYWRNRVLKVAKEFVGQINFAIASK
SEQ ID NO:10     HGLVGHRTHDNHDDFEKAPLIVVYYDVDYDYVKNVKGTNYWRNRVMKVAQNYKGQVNFAISNK
SEQ ID NO:12     HGLVGHRTSDNFQDFKNPLVVAYYDVDYVKNTKGTNYWRNRIMKVAQHFKDKLNFAVSNI
SEQ ID NO:14     HGLVGHRTTDNTNQFSPPLIVSYYKVDYVKNTKGTNYWRNRIMKVASEFKGRLNFAISNK
                 241                                                          300

*          ****   *   *** +    *+* **+     ++ *  + +++   *
SEQ ID NO:29     DDFQHELNEYGYDFV-GDKPVVLARDEKNLKYALKDEFSVENLQDFVEKLLANELEPYIK
SEQ ID NO:10     DKFSAEVEDFGLK-ATGDKPVVAARNDKNQKEFNMKEEFSVENFETFVKKFLDGSLEPHLK
SEQ ID NO:12     NQFSAEIEEFGLT-VKGDKPAIAVRNEKQQKFRMTDEFSMDAFEKFLKDFLDGKLEAHVK
SEQ ID NO:14     DEFTHELSEYGFNYVAGDKPVVAARNAKSEKFVMEGEFSIPSFEKFIKDFLDEKLKPYLK
                 301                                                          360

*** ***  *   *********    *        *        *** **++  *  *** *
SEQ ID NO:29     SEPIPESNDAPVKVAVAKNFDDLVINNGKDTLIEFYAPWCGHCKKLTPIYEELAQKLQDE
SEQ ID NO:10     SEPVPEKNDGPVKVAVAQNFEELVMENDKDVLIEFYAPWCGHCKKLAPTYEELGQKLEGE
SEQ ID NO:12     SEPIPENNDGPVKVAVASNFDDIVTNNDKDILLEFYAPWCGHCKKLAPTYEELGTEMKQE
SEQ ID NO:14     SEPIPEKNEEPVKVAVAQNFEELVTKSDKDVLIEFYAPWCGHCKKLAPVYDELGKALEGE
                 361                                                          420

+  ***************  +*+**********   *   *****    *  *    *
SEQ ID NO:29     D-VAIVKMDATANDVPPEFNVRGFPTLFWLPKDAKNKPVSYNGGREVDDFLKYIAKEATT
SEQ ID NO:10     D-VEIVKMDATANDVPPTFEVHGFPTLYWVPKTHKSSPKKYEGGREIKDFINYIAKHATN
SEQ ID NO:12     D-VEIVKMDATANDVPPPYEVHGFPTLYWPKNSKNNPKKYDGGRELDDLIKYISKHATN
SEQ ID NO:14     TTVEIVKMDATANDVPSPYEVHGFPTLYWAPRDKKDKPVRYDGGRELDDFIKYIAKHSTD
                 421                                                          480
```

Figure 2C

```
                      *** *     *  *+*     *  ***
SEQ ID NO:29          ELKGFDRSGKPK--KTEL
SEQ ID NO:10          ELKQYDRSGKKKS-KEEL
SEQ ID NO:12          ELKGWDRKGTKKSEKTEL
SEQ ID NO:14          ELKTYNRNGKKK--KVEL
                      481               498
```

Figure 3A

```
                 ++++++++    +++++++++++++++++++++++++++++++++++++++++++++++++++
SEQ ID NO:30     MLRRALLCLAVAALVRADAPEEEDHVLVLRKSNFAEALAAHKYLLVEFYAPWCGHCKALA
SEQ ID NO:16     MNFGNLLIF-FSFLIVVLGEVREDNVLVLNKENFDHSIKNNKYILVEFYAPWCGHCKALA
SEQ ID NO:18     MNFGNLLIF-FSFLIVVLGEVREDNVLVLNKENFDHSIKNNKYILVEFYAPWCGHCKALA  60
                 1

********  +++++++++++++++++++++++++++   +++  ++++++++
SEQ ID NO:30     PEYAKAAGKLKAEGSEIRLAKVDATEESDLAQQYGVRGYPTIKFFRNGDTASPKEYTAGR
SEQ ID NO:16     PEYAKAAKLLEEKSEIQLAKIDATEETELAEKHKVKGYPTIKFFREGD---PIDYTGGR
SEQ ID NO:18     PEYAKAAKLLEEKSEIQLAKIDATEETELAEKHKVKGYPTIKFFREGD---PIDYTGGR  120
                 61

++++++++++++++++++++++++++++++++++++ +++++++++++++++++++++
SEQ ID NO:30     EADDIVNWLKKRTGPAATTLPDGAAAESLVESSEVAVIGFFKDVESDSAKQFLQAAEAID
SEQ ID NO:16     TGDDIVTWLKKKTGPPATLLSTVDEATNFKESKDVVIIGFFKDQESNQAKEYLNAAYMTD
SEQ ID NO:18     TGDDIVTWLKKKTGPPATLLSTVDEATNFKESKDVVIIGFFKDQESNQAKEYLNAAYMTD  180
                 121

++++++++   +++++++++++++++++++++++ +++++++++++++++++++++++
SEQ ID NO:30     DIPFGITSNSDVFSKYQLDKDGVVLFKKFDEGRNNFEGEVTKENLLDFIKHNQLPLVIEF
SEQ ID NO:16     DHPFGITSDENVYKHFNVEKDTIFLFKKFDEGKNEFEGFTKDNIIKFIKLNNLPLVIEF
SEQ ID NO:18     DHPFGITSDENVYKHFNVEKDTIFLFKKFDEGKNEFEGFTKDNIIKFIKLNNLPLVIEF  240
                 181

++++++++ ++++++++++++++++++++++++++++++++++++++++++++++ *
SEQ ID NO:30     TEQTAPKIFGGEIKTHILLFLPKSVSDYDGKLSNFKTAAESFKGKILFIFIDSDHTDNQR
SEQ ID NO:16     SQENAQKIFGGDIKMHNLLFISKKSKDFDEIVKTFRIVAKEYKNQILFVVINTDEDNEK
SEQ ID NO:18     SQENAQKIFGGDIKMHNLLFISKKSKDFDEIVKTFRIVAKEYKNQILFVVINTDDEGNGQ  300
                 241
```

Figure 3B

```
                         *+*+***********+++++++++++++++++++++*+******+++++++
SEQ ID NO:30   ILEFFGLKKEECPAVRLITLEEMTKYKPESEELTAERITEFCHRFLEGKIKPHLMSQEL
SEQ ID NO:16   ITEFFGLKKDEQPSIRLIKLEEGMSKYKPETIEISEENVRKFVKGVLDGTVKQHLLSQEL
SEQ ID NO:18   ITEFFGLKKDEQPSIRLIKLEEGMSKYKPETIEISEENVRKFVKGVLDGTVKQHLLSQEL
                                                                       360
                                                                       301

*+*****+++**+***+*+*+++++++++++++++++++++++++***+++++++++
SEQ ID NO:30   PEDWDKQPVKVLVGKNFEDVAFDEKKNVFVEFYAPWCGHCKQLAPIWDKLGETYKDHENI
SEQ ID NO:16   PEDWDKHPVKVLVNKNFDEVAFDKTKDVIVEFYAPWCGHCKQLAPIYEELGEKYKNRNDI
SEQ ID NO:18   PEDWDKHPVKVLVNKNFDEVAFDKTKDVIVEFYAPWCGHCKQLAPIYEELGEKYKNRNDI
                                                                       420
                                                                       361

+*+***+**+****++***+++++  +*+***+*+*+**+*+**+++++++++*+++
SEQ ID NO:30   VIAKMDSTANEVEAVKVHSFPTLKFFPASADRTVIDYNGERTLDGFKKFLESGGQDGAGD
SEQ ID NO:16   IIAKMDATANELEHTKINSFPTIKLYKKGTN-EVIDYDGKHSLEGLVNFIDSGGKIT---
SEQ ID NO:18   IIAKMDATANELEHTKINSFPTIKLYKKGTN-EVIDYDGKHSLEGLVNFIDSGGKIT---
                                                                       480
                                                                       421

+*+**+*+++++++++   ***
SEQ ID NO:30   DDDLEDLEEAEEPDMEEDDDQKAVKDEL
SEQ ID NO:16   ------KEPEDEDKSKEPDAK--GDEL
SEQ ID NO:18   ------KEPEDEDKSKEPDAK--RDEL
                                                                       508
                                                                       481
```

Figure 4A

```
SEQ ID NO:31                                                                        *   ***
SEQ ID NO:32   MK---MEMHQIWSRIALASFAFAILFVSSADDVVLTEENFEKEVGHDKGA-LVEFYAP
SEQ ID NO:20   S-C------TFFLAVS------ALYS--SSDDVIELTPSNFNREVIQSDSLWLVEFYAP
SEQ ID NO:22   MGCYLLVLILFLF-FLRDSQSSSDLYT----DNSIKYDEEGFRRNIGN-IVH-FVKFYAP
SEQ ID NO:24   H-------------------------------------------------------
SEQ ID NO:26   -----TRLSSVFSFNVAIYASSDLYV----DNSLKYDEDGFRENVGK-LTL-FVKFYAP
               MLH------TYFLGILLCVGSGLALYD--SSSDVVDLTPDNFYQLVTDRDDVWLVEFYAP
                 1                                                        60

*****  *       *                  *   *   **    *  * ***
SEQ ID NO:31   WCGHCKKLAPEYEKLPNSFK---KAKSVLIAKVDCDEHKSVCSKYGVSGYPTIQWFPKGS
SEQ ID NO:32   WCGHCQRLTPEWKKAASALK------DVVKVGAVNADKHQSLGGQYGVQGFPTIKIFGANK
SEQ ID NO:20   WCGHCKRLAPIWDELAEKYN-KPGEQKLVIAKIDCTTETALCSEQGITGYPTLKFFKKGT
SEQ ID NO:22   ------------------------------------------------------------
SEQ ID NO:24   WCGHCKRLAPTWDELAEKYNIQPEKQQVIIAKIDCTSETALCSEQIGTYPTLKFFKKGE
SEQ ID NO:26   WCGHCKNLVPEYKKAAKALK----GIVKVGAIDADKHRSFAKDYGVSGFPTIKIFTGRK
                61                                                        120

*   *                                     +  *          *
SEQ ID NO:31   LEPKKFEGPRTAES--------LAEFV------NTEGG--TNVKIATAP---SHVVVLTPE
SEQ ID NO:32   NKPEDYQGGRTGEAIVDAALSALRQLVKDRLGGRSGGYSSGKQGRGDSSSKKDVVELTDD
SEQ ID NO:20   TEGHKYRGPRDITS--------LEAFIANSLGHEEAI--K--KSPEPPKFINEIIQLSDN
SEQ ID NO:22   ---------------------------EKP------DRSSEKS-DSDVITLTDE
SEQ ID NO:24   TEGTKYRGPRDITS--------LEAFIANSLGKEEAV--EDLKPPEP---VNGLIELTDE
SEQ ID NO:26   HVP--YKGARSADAFVDAALSAVKSKAYERLGKRS-------DDSSHKSSDSDVITLTDD
               121                                                        180
```

Figure 4B

```
                  *          *    * **********   *          *        *                *
SEQ ID NO:31      TFNEVVLDGTKDVLVEFYAPWCGHCKSLAPIYEKVAAVFKSEDD--VVIANLDADKYRDL
SEQ ID NO:32      TFDKNVLDSEDVWMVEFYAPWCGHCKNLEPEWAAAATEVKEQTKGKVKLAAVDATVNQVL
SEQ ID NO:20      TEHKFVAKGLH--FVKFYAPWCGHCQKLVPIWKELANSFKFDTS--IKISEIDCTTQHLV
SEQ ID NO:22      NFKKLVLDSEDLWLVEFYAPWCGHCNLKPQWAKAAKELK----GKVKLGALDATVHQAM
SEQ ID NO:24      TFHKTIERGYH--FVKFYAPWCGHCQKLAPVWQQLANSFQHDLS--VKILKIDCTAHRLS
SEQ ID NO:26      NFKKLVLDSDDLWLVEFFAPWCGHCKNLEPHWAKAAATELK----GKVKVGALDATVHQEM
                  181                                                          240

*       *                    +*  *      *   *  **
SEQ ID NO:31      AEKYDVSGFPTLKFFPKGNKA---GEDYGGGRDLDDFVAFINE--KSGTSRDAKGQLTSE
SEQ ID NO:32      ASRYGIKGFPTIKIFQKG----ESPVDYDGGRTRSDIVSRALDLFSDNAPPELLEIINE
SEQ ID NO:20      CNEFEVKAYPTLLWIVDGKKI----EKYEGMR---------------------------
SEQ ID NO:22      ASRYQVQGYPTIKLFPSGKKSSDSAEDYNGGRTASDIVTYALDKLAENVPAPEIVQVIDE
SEQ ID NO:24      CNEFEVKAYPTLLWIVDGKKV----EIYQGSRTHEDLKLFVDKMRRQEHETDSGGEHGKI
SEQ ID NO:26      AGRFQVQGYPTIKYFPSGKKTYDSAEDYNGGRTSSDIVSFALEKLAENVPAPEIIQVVNE
                  241                                                          300

SEQ ID NO:31      AGIVEDLDE-------LVKEFVAANDEKK--AVFARIEEEVKK-----------------
SEQ ID NO:32      DIAKKTCEEHQLCVVALVLPHILDTGATGRNSYLEVLLKLADKYKKKMWGWLWTEAGAQYE
SEQ ID NO:20      ------------------------------------------------------------
SEQ ID NO:22      A-SMQACSEKPLCVVSVLPHILDCNAACRNEYLAILARLGDKYKSKMWGWVAEAGAQIS
SEQ ID NO:24      PESLPKPEA-----PVAQLVASNFED-----SIKNGVTF--------------------
SEQ ID NO:26      A-TMQACSEKPLCVVSVLPHIFDCNAACRNDYLAILARLGDKYKNKMWGWVAEAGAQLG
                  301                                                          360
```

Figure 4C

```
SEQ ID NO:31   LEGSASRYGKIYLKVSKK-----YLEKGSDYAKNEIQRLERLLE--------K
SEQ ID NO:32   LENALGIGGFGYPAMAAINARKMKFALLKGSFSEQGINEFLRELSFGRGSTAPVGGGSFP
SEQ ID NO:20   ------------------------------------------------------
SEQ ID NO:22   LEESLELGGFGYPAMAVVNAKKLKFSTLRGSFSETGINEFLRDLSFGRGQTAPVKGAEMP
SEQ ID NO:24   VKFFAPWCGH-CRKLAPI------WDELSWEFIDNENGKIAQ-------------
SEQ ID NO:26   LEESLELGGFGYPAMAVVNAKKLKFSTLRGSFSETGINEFLRDLSFGRGQTAPVRGAEMP
               361                                                        420

SEQ ID NO:31   SISPA----KADELTLKKNI-LSTYA-----------------
SEQ ID NO:32   NITPREPWDGKDGELPVEDDIDLSDVELDDLEKDEL
SEQ ID NO:20   ------------------------------------
SEQ ID NO:22   KIVSTDPWDGKDGELPQEEDIDLSDV---DLEKDEL
SEQ ID NO:24   -VDCS-----SQESLCSK------------------
SEQ ID NO:26   KIVSTDAWDGKDGELPQEEDIDLSDV---DLEKDEL
               421                              456
```

ARTHROPOD PROTEIN DISULFIDE ISOMERASES

This application claims the benefit of U.S. Provisional Application No. 60/104376, filed Oct. 15, 1998.

FIELD OF THE INVENTION

This invention is in the field of molecular biology. More specifically, this invention pertains to nucleic acid fragments encoding arthropod protein disulfide isomerases.

BACKGROUND OF THE INVENTION

Protein folding requires the assistance of folding helpers in vivo. The formation or isomerization of disulfide bonds in proteins is a slow process requiring catalysis. In nascent polypeptide chains the cysteine residues are in the thiol form. The formation of the disulfide bonds usually occurs simultaneously with the folding of the polypeptide, in the endoplasmic reticulum of eukaryotes or in the periplasm of Gram-negative bacteria. Cells contain three types of accessory proteins that function to assist polypeptides in folding to their native conformations: protein disulfide isomerases, propyl cis-trans isomerases, and molecular chaperones.

Protein disulfide isomerase (PDI) is a homodimeric eukaryotic enzyme which catalyzes disulfide interchange reactions. PDI is also thought to be the beta subunit of the heterotetramer prolyl hydrolase, the enzyme that hydroxylates the proline residues in Collagen. PDI appears to belong to a family of closely related proteins which have specific functions. PDI (EC 5.3.4.1), also called S-S rearrangase, catalyzes the rearrangement of both intrachain and interchain disulfide bonds in proteins to form native structures. The reaction depends on sulfhydryldisulfide interchange, and PDI needs reducing agents or partly-reduced enzyme. A family of PDI-like proteins have been identified in mammals, yeasts, fungi, plants, and Drosophila.

In Drosophila, a PDI precursor was identified by screening a genomic DNA library at reduced stringency hybridization conditions using a rat Phospholipase C alpha cDNA probe. Northern analysis showed that this gene encodes a transcript that is present throughout development, in heads and bodies of adults. The encoded protein contains two domains exhibiting high similarity to thioredoxin, two regions that are similar to the hormone binding domain of human estrogen receptor, and a C-terminal ER-retention signal (KDEL). Overall, this Drosophila PDI gene contains a higher similarity to rat protein disulfide isomerase (53% identical) than to rat Phospholipase C alpha (30% identical) (McKay et al. (1995) *Insect Biochem Mol Biol* 25:647–654).

Another member of the PDI family is ERp-60, a PDI isoform initially misidentified as a phosphatidylinositol-specific phospholipase C. The human and Drosophila ERp60 polypeptides have been cloned and expressed. These two ERp-60 polypeptides are similar to human PDI within almost all their domains, the only exception being the extreme C-terminal region. Coexpression in insect cells of the human or Drosophila ERp-60 with the alpha subunit of human propyl 4-hydrolase does not result in tetramer formation or prolyl 4-hydroxylase activity in the cells. This lack of tetramer formation is not only due to the differences in the C-terminal region since no prolyl 4-hydroxylase tetramer is formed when a human ERp-60 hybrid containing the C-terminal region of the human PDI polypeptide is used (Koivunen et al. (1996) *Biochem J* 316:599–605). The 5' flanking region of the ERp-60 gene has no TATAA box or CCAAT motif but contains several potential binding sites for transcription factors. The highest levels of expression of the human ERp-60 mRNA are found in the liver, placenta, lung, pancreas, and kidney, and the lowest in the heart, skeletal muscle, and brain. The ERp-60 gene has been mapped by fluorescence in situ hybridization to 15q15, a different chromosome than where the human PDI and thioredoxin genes are found (Koivunen, et al. (1997) *Genomics* 42:397–404).

Full-length cDNA clones encoding two members of the mice PDI family have been cloned, sequenced, and expressed (ERp-59/PDI and ERp-72). ERp-59/PDI has been identified as the microsomal PDI. The ERp-72 amino acid sequence shares sequence identity with ERp-59/PDI at three discrete regions, having three copies of the sequences that are thought to be the CGHC-containing active sites of ERp-59/PDI. ERp-59/PDI has the sequence KDEL at its COOH terminus while ERp72 has the related sequence KEEL (Mazarella et al. (1990) *J Biol Chem* 265:1094–1101). A cDNA clone containing sequence similarity to the mammalian lumenal endoplasmic reticulum protein ERp-72 has been isolated from an alfalfa (*Medicago sativa L.*) cDNA library by screening with a cDNA encoding human PDI. The polypeptide encoded by this cDNA possesses a putative N-terminal secretory signal sequence and two regions identical to the active sites of PDI and ERp-72. This protein appears to be encoded by a small gene family in alfalfa, whose transcripts are constitutively expressed in all major organs of the plant. In alfalfa cell suspension cultures, ERp-72 transcripts are induced by treatment with tunicamycin, but not in response to calcium ionophore, heat shock or flingal elicitor (Shorrosh and Dixon (1992) *Plant J* 2:51–58)

Another member of the PDI family is ERp-5. The amino acid sequence deduced from its cDNA insert contains two copies of the 11-amino-acid sequence Val-Glu-Phe-Tyr-Ala-Pro-Trp-Cys-Gly-His-Cys. Duplicate copies of this sequence are found in the active sites of rat and human PDI and in Form I phosphoinositide-specific phospholipase C. Genomic sequences similar to the cDNA clone are amplified 10–20-fold in hamster cells selected for resistance to increasing concentrations of hydroxyurea, a phenomenon observed earlier with cDNA clones for the M2 subunit of ribonucleotide reductase and ornithine decarboxylase. RNA blots probed with ERp-5 cDNA show two poly(A)+ RNA species which are elevated in hydroxyurea-resistant cells (Chaudhuri et al. (1992) *Biochem J* 281:645–650).

A PDI-like protein from *Acanthamoeba castellanii* contains two highly conserved thioredoxin-like domains, each about 100 amino acids. However, the *A. castellanji* PDI-like protein differs from other members in many aspects, including the overall organization and isoelectric point. Southern and Northern analyses demonstrate that the PDI-like protein is encoded by a single-copy gene which is transcribed to generate a 1500-nucleotide mRNA (Wong and Bateman (1994) *Gene* 150:175–179).

Included in this application are scorpion, spider, lepidoptera, and centepede ESTs with similarities to several of these PDIs. Coexpression in plants or insect cells of an arthropod PDI with a secreted arthropod protein should enhance the yield of the foreign protein by increasing the proper folding of the foreign protein.

SUMMARY OF THE INVENTION

The present invention relates to isolated polynucleotides comprising a nucleotide sequence encoding a protein disulfide isomerase precursor polypeptide of at least 50 amino acids that has at least 80% identity based on the Clustal method of alignment when compared to a polypeptide selected from the group consisting of a spider, a centipede, a moth, and a scorpion protein disulfide isomerase of SEQ ID NOs:2, 4, 6, and 8. The present invention also relates to isolated polynucleotides comprising a nucleotide sequence encoding an ERp60 polypeptide of at least 50 amino acids that has at least 80% identity based on the Clustal method of alignment when compared to a polypeptide selected from the group consisting of a spider, a centipede, and a scorpion ERp60 of SEQ ID NOs:10, 12, and 14. The present invention also relates to isolated polynucleotides comprising a nucleotide sequence encoding an ERp72 polypeptide of at least 50 amino acids that has at least 80% identity based on the Clustal method of alignment when compared to a polypeptide selected from the group consisting of a two scorpion ERp72s of SEQ ID NOs:16 and 18. The present invention also relates to isolated polynucleotides comprising a nucleotide sequence encoding an ERp5 polypeptide of at least 50 amino acids that has at least 80% identity based on the Clustal method of alignment when compared to a polypeptide selected from the group consisting of a moth, a worm, and two scorpion ERp5s of SEQ ID NOs:20, 22, 24, and 26. The present invention also relates to an isolated polynucleotide comprising the complement of the nucleotide sequences described above.

It is preferred that the isolated polynucleotide of the claimed invention consists of a nucleic acid sequence selected from the group consisting of SEQ ID NOs:1, 3, 5, 7, 9,11, 13, 15,17,19, 21, 23, and 25 that codes for the polypeptide selected from the group consisting of SEQ ID NOs:2, 4, 6, 8,10, 12,14, 16,18, 20, 22, 24, and 26. The present invention also relates to an isolated polynucleotide comprising a nucleotide sequence of at least 40 (preferably at least 30) contiguous nucleotides derived from a nucleotide sequence selected from the group consisting of SEQ ID NOs:1, 3, 5, 7, 9,11,13,15,17,19, 21, 23, 25 and the complement of such nucleotideqsequences.

The present invention relates to a chimeric gene comprising an isolated polynucleotide (such as ERp-60, an ERp-72, an ERp-5, or a PDI-like homolog) of the present invention operably linked to suitable regulatory sequences.

The present invention relates to an isolated host cell comprising a chimeric gene of the present invention or an isolated polynucleotide of the present invention. The host cell may be of eukaryotic origin, such as an insect, a yeast, or a plant cell; of prokaryotic origin, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a protein disulfide isomerase precursor polypeptide of at least 30 amino acids comprising at least 80% homology based on the Clustal method of alignment compared to a polypeptide selected from the group consisting of SEQ ID NOs:2, 4, 6, and 8. The present invention relates to an ERp60 polypeptide of at least 40 amino acids comprising at least 80% homology based on the Clustal method of alignment compared to a polypeptide selected from the group consisting of SEQ ID NOs:10, 12, and 14. The present invention relates to an ERp72 polypeptide of at least 20 amino acids comprising at least 80% homology based on the Clustal method of alignment compared to a polypeptide selected from the group consisting of SEQ ID NOs:16 and 18. The present invention relates to an ERp5 polypeptide of at least 50 amino acids comprising at least 80% homology based on the Clustal method of alignment compared to a polypeptide selected from the group consisting of SEQ ID NOs:20, 22, 24, and 26.

The present invention relates to a method of selecting an isolated polynucleotide that affects the level of expression of a protein disulfide isomerase polypeptide in a host cell, the method comprising the steps of:

constructing an isolated polynucleotide of the present invention or an isolated chimeric gene of the present invention;

introducing the isolated polynucleotide or the isolated chimeric gene into a plant cell;

measuring the level an enzyme polypeptide in the plant cell containing the isolated polynucleotide; and comparing the level of an enzyme polypeptide in the plant cell containing the isolated polynucleotide or an isolated chimeric gene with the level of an enzyme polypeptide in a plant cell that does not contain the isolated polynucleotide or an isolated chimeric gene.

presentinvention relates to a method of obtaining a nucleic acid fragment encoding a substantial portion of a protein disulfide isomerase polypeptide gene, preferably an arthropod polypeptide gene, comprising the steps of: synthesizing an oligonucleotide primer comprising a nucleotide sequence of at least 40 (preferably at least 30) contiguous nucleotides derived from a nucleotide sequence selected from the group consisting of SEQ ID NOs:1, 3, 5, 7, 9, 11, 13, 15, 17, 19, 21, 23, and the complement of such nucleotide sequences; and amplifying a nucleic acid fragment (preferably a cDNA inserted in a cloning vector) using the oligonucleotide primer. The amplified nucleic acid fragment preferably will encode a portion of a protein disulfide isomerase amino acid sequence.

The present invention also relates to a method of obtaining a nucleic acid fragment encoding all or a substantial portion of the amino acid sequence encoding a protein disulfide isomerase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

The instant invention relates to isolated nucleic acid fragments encoding arthropod protein disulfide isomerases. Specifically, this invention concerns an isolated nucleic acid fragment encoding an ERp-60, an ERp-72, an ERp-5, or a PDI-like homolog. In addition, this invention relates to a nucleic acid fragment that is complementary to the nucleic acid fragment encoding ERp-60, ERp-72, ERp-5, or PDI-like homolog.

Another embodiment of the instant invention pertains to a method for expressing a gene encoding a protein disulfide isomearase in the genome of a recombinant baculovirus in insect cell culture or in viable insects wherein said insect cells or insects have been genetically engineered to express an ERp-60, an ERp-72, an ERp-5, or a PDI-like homolog.

BRIEF DESCRIPTION OF THE DRAWINGS AND SEQUENCE LISTING

The invention can be more fully understood from the following detailed description and the accompanying drawings and Sequence Listing which form a part of this application.

FIGS. 1A, 1B and 1C show a comparison of the amino acid sequences of the protein disulfide isomerase precursors of the instant invention (SEQ ID NOs:2, 4, 6, and 8) with the sequences of protein disulfide isomerase precursors from Drosophila melanogaster (NCBI General Identifier No.1709616; SEQ ID NO:27) and Gallus gallus (NCBI General Identifier No. 2144546; SEQ ID NO:28). The top row indicates with asterisks (*) the amino acids which are conserved among all the sequences from the instant invention and one or both of the art sequences. The top row indicates with plus signs (+) the sequences which are conserved only among the sequences from the instant invention.

FIGS. 2A, 2B, and 2C show a comparison of the amino acid sequences of the ERp60 of the instant invention (SEQ ID NOs:10, 12, and 14) with the sequence of ERp60 from Drosophila melanogaster(NCBI General Identifier No.1699220; SEQ ID NO:29). The top row indicates with asterisks (*) the amino acids which are conserved among all the sequences. The top row indicates with plus signs (+) the sequences which are conserved only among the sequences from the instant invention.

FIGS. 3A and 3B show a comparison of the amino acid sequences of the ERp72 of the instant invention (SEQ ID NOs:16 and 18) with the sequence of ERp72 from Homo sapiens (NCBI General Identifier No. 2507460; SEQ ID NO:30). The top row indicates with asterisks (*) the amino acids which are conserved among all the sequences and with plus signs (+) the sequences which are conserved only among the arthropod sequences.

FIGS. 4A, 4B and 4C show a comparison of the amino acid sequences of the ERp5 of the instant invention (SEQ ID NOs:20, 22, 24, and 26) with the sequences of ERp5 from *Medicago sativa* (NCBI General Identifier No. 729442; SEQ ID NO:31) and *Rattus norvegicus* (NCBI General Identifier No. 2501206; SEQ ID NO:32). The top row indicates with asterisks (*) the amino acids which are conserved among all the arthropod sequences and one or both of the art sequences. The top row indicates with plus signs (+) the sequences which are conserved only among the arthropod sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

| Protein Disulfide Isomerases | | | |
|---|---|---|---|
| | Clone | SEQ ID NO: | |
| Protein | Designation | (Nucleotide) | (Amino Acid) |
| Spider Protein Disulfide Isomerase Precursor | aot1c.pk016.k11 | 1 | 2 |
| Centipede Protein Disulfide Isomerase Precursor | asc1.pk033.i19 | 3 | 4 |
| Moth Protein Disulfide Isomerase Precursor | ihv1c.pk001.h12 | 5 | 6 |

TABLE 1-continued

| Protein Disulfide Isomerases | | | |
|---|---|---|---|
| | Clone | SEQ ID NO: | |
| Protein | Designation | (Nucleotide) | (Amino Acid) |
| Scorpion Protein Disulfide Isomerase Precursor | iks1c.pk0004.c12 | 7 | 8 |
| Spider ERp-60 | aot1c.pk011.n11 | 9 | 10 |
| Scorpion ERp-60 | ibj1c.pk015.k8 | 11 | 12 |
| Centipede ERp-60 | isc1c.pk009.m16 | 13 | 14 |
| Scorpion ERp-72 | ibj1c.pk008.d11 | 15 | 16 |
| Scorpion ERp-72 | ibj1c.pk014.c1 | 17 | 18 |
| Scorpion ERp-5 | ibj1c.pk015.o22 | 19 | 20 |
| Moth ERp-5 | ihv1c.pk001.a7 | 21 | 22 |
| Scorpion ERp-5 | iks1c.pk010.i14 | 23 | 24 |
| Worm ERp-5 | ise1c.pk002.m4 | 25 | 26 |

The Sequence Listing contains the one letter code for nucleotide sequence characters and the three letter codes for amino acids as defined in conformity with the IUPAC-WUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least 40 contiguous nucleotides, preferably at least 30 contiguous nucleotides, most preferably at least 15 contiguous nucleotides, of the nucleic acid sequence of the SEQ ID NOs:1, 3, 5, 7, 9, 11, 13, 15, 17, 29, 21, 23 and 25.

"NPV" stands for Nuclear Polyhedrosis Virus, a baculovirus. "Polyhedrosis" refers to any of several virus diseases of insect larvae characterized by dissolution of tissues and accumulation of polyhedral granules in the resultant fluid. "PIBs" are polyhedral inclusion bodies. "AcNPV" stands for the wild-type *Autographa californica* Nuclear Polyhedrosis Virus.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of one or more nucleotides that do not substantially affect the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a host or host cell. For example, a substantially similar nucleic acid fragment representing at least 30 contiguous nucleotides derived from theinstant nucleic acid fragment can be constructed and introduced into a host or host cell. The level of the polypeptide encoded by the unmodified nucleic acid fragment present in a host or host cell exposed to the substantially similar nucleic fragment can then be compared to the level of the polypeptide in a host or host cell that is not exposed to the substantially similar nucleic acid fragment.

Consequently, an isolated polynucleotide comprising a nucleotide sequence of iat least 40 (preferably at least 30, most preferably at least 15) contiguous nucleotides derived from a nucleotide sequence selected from the group consisting of SEQ ID NOs:1, 3, 5, 7, 9, 11, 13, 15, 17, 19, 21, 23, 25 and the complement of such nucleotide sequences may be used in methods of selecting an isolated polynucleotide that affects the expression of a polypeptide in a host cell. A method of selecting an isolated polynucleotide that affects the level of expression of a polypeptide (such as a disulfide isomerase, Erp 60, Erp 72, or Erp 5) in a host cell (eukaryotic, such as plant, insect, or yeast; prokaryotic such as bacterial; viral such as baculovirus) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of the polypeptide in the host cell containing the isolated polynucleotide with the level of the polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 2×SSC, 0.5% SDS at 50° C. for 30 min. A more preferred set of stringent conditions uses igher temperatures in which the washes are identical to those above except for the emperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are 80% identical to the amino acid sequences reported herein. Preferred nucleic acid fragments encode amino acid sequences that are 85% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Suitable nucleic acid fragments not only have the above homologies but typically encode a polypeptide having at least 50 amino acids, preferably 100 amino acids, more preferably 150 amino acids, still more preferably 200 amino acids, and most preferably 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY= 10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) J. Mol. Biol. 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in a variety of cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' nonoding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Functional RNA" refers to sense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Overexpression" refers to the production of a gene product in transgenic organisms that exceeds levels of production in normal or non-transformed organisms.

"Altered levels" refers to the production of gene product (s) in transgenic organisms in amounts or proportions that differ from that of normal or non-transformed organisms.

A "signal sequence" is an amino acid sequence that is covalently linked to an amino acid sequence representing a mature protein. The signal sequence directs the protein to the secretory system (Chrispeels (1991) *Ann Rev. Plant Phys. Plant Mol. Biol.* 42:21–53). "Mature" protein refers to a post-translationauy processed polypeptide; i.e., one from which any pre- or propeptides, including signal sequences, present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

It is understood that "an insect cell" refers to one or more insect cells maintained in vitro as well as one or more cells found in an intact, living insect.

Standard recombinant DNA and molecular cloning techniques used herein are well known in the art and are described more fully in Sambrook et al. Molecular Cloning: A Laboratory Manual; Cold Spring Harbor Laboratory Press: Cold Spring Harbor, 1989 (hereinafter "Maniatis").

Nucleic acid fragments encoding at least a portion of several protein disulfide isomerases have been isolated and identified by comparison of cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other arthropod species. Isolation of homologous genes using sequence-dependent protocols is well known in the art. Exanples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other ERp-60s, ERp-72s, ERp-5s, or PDI-like homologs, either as cDNAs or genomic DNAs, could be isolated directly by using all or a portion of the instant nucleic acid fragments as DNA hybridization probes to screen libraries from any desired arthropod employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding arthropod genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 40 (preferably one of at least 30, most preferably one of at least 15) contiguous nucleotides derived from a nucleotide sequence selected from the group consisting of SEQ ID NOs:1, 3, 5, 7, 9, 11, 13, 15, 17, 19, 21, 23, 25 and the complement of such nucleotide sequences may be used in such methods to obtain a nucleic acid fragment encoding a substantial portion of an amino acid sequence of a polypeptide such as a protein disulfide isomerase. The present invention relates to a method of obtaining a nucleic acid fragment encoding a substantial portion of a polypeptide of a gene (such as ERp-60, an ERp-72, an ERp-5, or a PDI-like homolog) preferably a substantial portion of an arthropod polypeptide of a gene, comprising the steps of: synthesizing an oligonucleotide primer comprising a nucleotide sequence of at least 40 (preferably at least 30, most preferably at least 15) contiguous nucleotides derived from a nucleotide sequence selected from the group consisting of SEQ ID NOs:1, 3, 5, 7, 9, 11, 13, 15, 17, 19, 21, 23, 25 and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide such as a protein disulfide isomerase.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lemer (1984) *Adv. Immunol.* 36:1–34; Maniatis).

The nucleic acid fragments of the instant invention may be used to create transgenic plants in which the disclosed protein disulfide isomerases are expressed. This would be useful as a means for controlling insect pests by producing plants that are more insect-tolerant than the naturally occurring variety.

Expression in plants of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, LC-MS, or phenotypic analysis.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded protein disulfide isomerase. An example of a vector for high level expression of the instant polypeptides in a bacterial host is provided (Example 9).

Insecticidal baculoviruses have great potential to provide an environmentally benign method for agricultural insect pest control. However, improvements to efficacy are required in order to make these agents competitive with current chemical pest control agents. One approach for making such improvements is through genetic alteration of the virus. For instance, it may be possible to modify the viral genome in order to improve the host range of the virus, to increase the environmental stability and persistence of the virus, or to improve the infectivity and transmission of the virus. In addition, improving the rate at which the virus acts to compromise the infected insect would significantly enhance the attractiveness of insecticidal baculoviruses as adjuncts or replacements for chemical pest control agents. One method for increasing the speed with which the virus affects its insect host is to introduce into the baculovirus foreign genes that encode proteins that are toxic to the insect wherein death or incapacitation of the insect is no longer dependent solely on the course of the viral infection, but instead is aided by the accumulation of toxic levels of the foreign protein. The results are insecticidal recombinant baculoviruses.

Recombinant baculoviruses expressing the instant protein disulfide isomerase (or portions thereof) may be prepared by protocols now known to the art (e.g., Tomalski et al., U.S. Pat. No. 5,266,317, exemplifing neurotoxins from the insect-parasitic mites; McCutchen et al. (1991) *Bio/Technology* 9:848–852; Maeda et al. (1991) *Virology* 184:777–780, illustrating construction of a recombinant baculovirus expressing AaIT; also see O'Reilly et al. (1992) *Baculovirus Expression Vectors: A Laboratory Manual*, W. H. Freeman and Company, New York; King and Possee (1992) *The Baculovirus Expression System*, Chapman and Hall, London; U.S. Pat. No. 4,745,051). These methods of gene expression provide economical preparation of foreign proteins in a eukaryotic expression vector system, in many instances yielding proteins that have achieved their proper tertiary conformation and formed the proper disulfide bridges necessary for activity.

Commonly, the introduction of heterologous genes into the baculovirus genome occurs by homologous recombination between viral genomic DNA and a suitable "transfer vector" containing the heterologous gene of interest. These transfer vectors are generally plasmid DNAs that are capable of autonomous replication in bacterial hosts, affording facile genetic manipulation. Baculovirus transfer vectors also contain a genetic cassette comprising a region of the viral genome that has been modified to include the following features (listed in the 5' to 3' direction): 1) viral DNA comprising the 5' region of a non-essential genomic region; 2) a viral promoter; 3) one or more DNA sequences encoding restriction enzyme sites facilitating insertion of heterologous DNA sequences; 4) a transcriptional termination sequence; and 5) viral DNA comprising the 3' region of a non-essential genomic region. A heterologous gene of interest is inserted into the transfer vector at the restriction site downstream of the viral promoter. The resulting cassette comprises a chimeric gene wherein the heterologous gene is under the transcriptional control of the viral promoter and transcription termination sequences present on the transfer vector. Moreover, this chimeric gene is flanked by viral DNA sequences that facilitate homologous recombination at a non-essential region of the viral genome. Recombinant viruses are created by co-transfecting insect cells that are capable of supporting viral replication with viral genomic DNA and the recombinant transfer vector. Homologous recombination between the flanking viral DNA sequences present on the transfer vector and the homologous sequences on the viral genomic DNA takes place and results in insertion of the chimeric gene into a region of the viral genome that does not disrupt an essential viral function. The infectious recombinant virion consists of the recombined genomic DNA, referred to as the baculovirus expression vector, surrounded by a protein coat.

In a preferred embodiment, the non-essential region of the viral genome that is present on the transfer vector comprises the region of the viral DNA responsible for polyhedrin production. Most preferred is a transfer vector that contains the entire polyhedrin gene between the flanking sequences that are involved in homologous recombination. Recombination with genomic DNA from viruses that are defective in polyhedrin production (due to a defect in the genomic copy of the polyhedrin gene) will result in restoration of the polyhedrin-positive phenotype. This strategy facilitates identification and selection of recombinant viruses.

In another embodiment, baculoviral genomic DNA can be directly modified by introduction of a unique restriction enzyme recognition sequence into a non-essential region of the viral genome. A chimeric gene comprising the heterologous gene to be expressed by the recombinant virus and operably linked to regulatory sequences capable of directing gene expression in baculovirus-infected insect cells, can be constructed and inserted directly into the viral genome at the unique restriction site. This strategy eliminates both the need for construction of transfer vectors and reliance on homologous recombination for generation of recombinant viruses. This technology is described by Ernst et al. (Ernst et al. (1994) *Nuc. Acid Res.* 22: 2855–2856), and in WO 94/28114.

Recombinant baculovirus expression vectors suitable for delivering genetically encoded insect-specific protein disulfide isomerases require optimal gene expression for maximum efficacy. A number of strategies can be used by the skilled artisan to design and prepare recombinant baculoviruses wherein protein disulfide isomerase gene expression results in sufficient quantities of protein disulfide isomerase produced at appropriate times during infection in a functional form and available for binding to target cells within the insect host.

The isolated protein disulfide isomerase gene fragment may be digested with appropriate enzymes and may be inserted into the pTZ-18R plasmid (Pharmacia, Piscataway, N.J.) at the multiple cloning site using standard molecular cloning techniques. Following transformation of *E. coli* DH5αMCR, isolated colonies may be chosen and plasmid DNA prepared. Positive clones will be identified and sequenced with the commercially available forward and reverse primers.

*Spodopteraftugiperda cells* (Sf-9) may be propagated in ExCell®401 media (JRH Biosciences, Lenexa, Kans.) supplemented with 3.0% fetal bovine serum. Lipofectin® (50 μL at 0.1 mg/mL, Gibco/BRL) may be added to a 50 μL aliquot of the transfer vector containing the toxin gene of interest (500 ng) and linearized polyhedrin-negative AcNPV (2.5 μg, BaculogoldD viral DNA, Pharmigen, San Diego, Calif.). Sf-9 cells (approximate 50% monolayer) may be co-transfected with the viral DNA/transfer vector solution. The supernatant fluid from the co-transfection experiment may be collected at 5 days post-transfection and recombinant viruses may be isolated employing standard plaque purification protocols, wherein only polyhedrin-positive plaques will be selected (Granados and Lawler (1981) *Virology* 108:297–308).

To propagate the recombinant virus of interest, isolated plaques may be picked and suspended in 500 μL of ExCell® media supplemented with 2.5% fetal bovine serum. Sf-9 cells in 35 mM petri dishes (50% monolayer) may be inoculated with 100 μL of the viral suspension, and supernatant fluids collected at 5 days post infection. These supernatant fluids will be used to inoculate cultures for large scale propagation of recombinant viruses.

Expression of the encoded protein disulfide isomerase gene by the recombinant baculovirus will be confirmed using a bioassay, LCMS, or antibodies.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various spider, caterpillar, centipede, moth, and scorpion tissues were prepared. The characteristics of the libraries are described below.

TABLE 2 cDNA Libraries from Scorpion, Caterpillar, Centipede, Moth, and Spider

| Library | Tissue | Clone |
|---|---|---|
| aot1c | Ceplalothorax of orb spider collected from Texas | aot1c.pk011.n11 |
| aot1c | Ceplalothorax of orb spider collected from Texas | aot1c.pk016.k11 |
| asc1 | *Scolopendra canidens* DS milked venom glands | asc1.pk033.i19 |
| ibj1c | *Buthatus judaicus* Telsons 48-Hours Post Milking | ibj1c.pk008.d11 |
| ibj1c | *Buthatus judaicus* Telsons 48-Hours Post Milking | ibj1c.pk015.k8 |
| ibj1c | *Buthatus judaicus* Telsons 48-Hours Post Milking | ibj1c.pk015.o22 |
| ibj1c | *Buthatus judaicus* Telsons 48-Hours Post Milking | ibj1c.pk014.c1 |
| ihv1c | Tobacco budworm (*Heliothis virescens*) Whole Insect | ihv1c.pk001.a7 |
| ihv1c | Tobacco budworm (*Heliothis virescens*) Whole Insect | ihv1c.pk001.h12 |
| iks1c | Kentucky scorpion Telsons 48-Hours Post Milking | iks1c.pk0004.c12 |
| iks1c | Kentucky scorpion Telsons 48-Hours Post Milking | iks1c.pk010.i14 |
| isc1c | *Scolopendra canidens* Telsons 48-Hours Post Milking | isc1c.pk009.m16 |
| isc1c | Fall armyworm (*Spodoptera exigua*) Whole Insect | ise1c.pk002.m4 | cDNA libraries may be prepared by any one of many methods available. For example, the cDNAs may be introduced into plasmid vectors by first preparing the cDNA libraries in Unc-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pbluescript plasmids, or the insert eDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones

ESTs encoding protein disulfide isomerases were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Protein Disulfide Isomerase Precursor The BLASTX search using the EST sequences from clones listed in Table 3 revealed similarity of the polypeptides encoded by the cDNAs to protein disulfide isomerase precursor from *Drosophila melanogaster* or *Gallus gallus* (NCBI General Identifier Nos. 4262594, 1709616, and 2144546, respectively). Shown in Table 3 are the BLAST results for individual ESTs ("EST"), or the sequences of the entire cDNA inserts comprising the indicated cDNA clones ("FIS"):

TABLE 3

BLAST Results for Sequences Encoding Polypeptides Homologous to Protein Disulfide Isomerase Precursor

| Clone | Status | NCBI General Identifier No. | BLAST pLog Score |
| --- | --- | --- | --- |
| ao1c.pk016.k11 | FIS | 1709616 | 166.00 |
| asc1.pk033.i19 | FIS | 2144546 | 168.00 |
| ihv1c.pk001.h12 | EST | 1709616 | 56.00 |
| iks1c.pk0004.c12 | EST | 2144546 | 165.00 |

The data in Table 4 represents a calculation of the percent identity of the amino acid sequences set forth in SEQ ID NOs:2, 4, 6, and 8 and the *Drosophila melanogaster* and *Gallus gallus* sequences (NCBI General Identifier Nos. 1709616 and 2144546, respectively).

TABLE 4

Percent Identity of Amino Acid Sequences Deduced From the Nucleotide Sequences of cDNA Clones Encoding Polypeptides Homologous to Protein Disulfide Isomerase Precursor

| | Percent Identity to | |
| --- | --- | --- |
| SEQ ID NO. | 1709616 | 2144546 |
| 2 | 54.8 | 53.8 |
| 4 | 54.6 | 55.8 |
| 6 | 65.4 | 60.2 |
| 8 | 53.2 | 54.1 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a spider, a centipede, a moth and a scorpion PDI precursor. These sequences represent the first arthropod sequences encoding protein disulfide isomerase precursor.

Example 4

Characterization of cDNA Clones Encoding ERp-60

The BLASTX search using the EST sequences from clones listed in Table 5 revealed similarity of the polypeptides encoded by the cDNAs to ERp-60 from *Drosophila melanogaster* (NCBI General Identifier No. 1699220). Shown in Table 5 are the BLAST results for the sequences of the entire cDNA inserts comprising the indicated cDNA clones ("FIS"):

TABLE 5

BLAST Results for Sequences Encoding Polypeptides Homologous to ERp-60

| Clone | Status | BLAST pLog Score 1699220 |
| --- | --- | --- |
| ao1c.pk011.n11 | FIS | 170.00 |
| ibj1c.pk015.k8 | FIS | 153.00 |
| isc1c.pk009.m16 | FIS | 172.00 |

The data in Table 6 represents a calculation of the percent identity of the amino acid sequences set forth in SEQ ID NOs:10, 12 and 14 and the *Drosophila melanogaster* sequence (1699220).

TABLE 6

Percent Identity of Amino Acid Sequences Deduced From the Nucleotide Sequences of cDNA Clones Encoding Polypeptides Homologous to ERp-60

| SEQ ID NO. | Percent Identity to 1699220 |
| --- | --- |
| 10 | 56.2 |
| 12 | 55.4 |
| 14 | 55.3 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a spider, a scorpion, and a centipede ERp-60. These sequences represent the first arthropod sequences encoding ERp-60.

Example 5

Characterization of cDNA Clones Encoding ERp-72

The BLASTX search using the EST sequences from clones listed in Table 7 revealed similarity of the polypeptides encoded by the cDNAs to ERp-72 from Homo sapiens (NCBI General Identifier No. 2507460). Shown in Table 7 are the BLAST results for the sequences of the entire cDNA inserts comprising the indicated cDNA clones ("FIS"):

TABLE 7

BLAST Results for Sequences Encoding Polypeptides Homologous to ERp-72

| Clone | Status | BLAST pLog Score 2507460 |
| --- | --- | --- |
| ibj1c.pk005.d11 | FIS | 161.00 |
| ibj1c.pk014.c1 | FIS | 160.00 |

The data in Table 8 represents a calculation of the percent identity of the amino acid sequences set forth in SEQ ID NOs:16 and 18 and the Homo sapiens sequence (NCBI General Identifier No. 2507460).

TABLE 8

Percent Identity of Amino Acid Sequences Deduced From the Nucleotide Sequences of cDNA Clones Encoding Polypeptides Homologous to ERp-72

| SEQ ID NO. | Percent Identity to 2507460 |
| --- | --- |
| 16 | 53.8 |
| 18 | 53.6 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, UtNOW=5 and DIAGONALS SAVED=5. Sequence alignments and BLAST scores and probabilities indicate that the nucleic acid fragments comprising the instant cDNA clones encode two entire scorpion ERp-72. These sequences represent the first scorpion sequences encoding ERp-72.

Example 6

Characterization of cDNA Clones Encoding, ERD-5

The BLASTX search using the EST sequences from clones listed in Table 9 revealed similarity of the polypeptides encoded by the cDNAs to ERp-5 from Medicago saliva or Rattus norvegicus (NCBI General Identifier Nos. 729442 and 2501206, respectively). Shown in Table 9 are the BLAST results for individual ESTs ("EST"), or the sequences of the entire cDNA inserts comprising the indicated cDNA clones ("FIS"):

TABLE 9

BLAST Results for Sequences Encoding Polypeptides Homologous to ERp-5

| Clone | Status | NCBI General Identifier No. | BLAST pLog Score |
| --- | --- | --- | --- |
| ibj1c.pk015.o22 | FIS | 729442 | 38.00 |
| ihv1c.pk001.a7 | FIS | 2501206 | 105.00 |
| iks1c.pk010.i14 | EST | 729442 | 39.15 |
| ise1c.pk002.m4 | FIS | 2501206 | 147.00 |

The data in Table 10 represents a calculation of the percent identity of the amino acid sequences set forth in SEQ ID NOs:18, 20, 22, and 24 and the Medicago saliva and Rattus norvegicus sequences (NCBI General Identifier Nos. 729442 and 2501206, respectively).

TABLE 10

Percent Identity of Amino Acid Sequences Deduced From the Nucleotide Sequences of cDNA Clones Encoding Polypeptides Homologous to ERp-5

| | Percent Identity to | |
| --- | --- | --- |
| SEQ ID NO. | 729442 | 2501206 |
| 18 | 27.9 | 22.5 |
| 20 | 19.4 | 59.2 |
| 22 | 24.2 | 19.2 |
| 24 | 26.4 | 55.6 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a caterpillar, a moth, and two scorpion ERp-5. These sequences represent the first arthropod sequences encoding ERp-5.

Example 7

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (Nco I or Sma I) can be incorporated into the oligonucleotides to provide proper orientation of the DNA fragment when inserted into the digested vector pML103 as described below. Amplification is then performed in a standard PCR. The amplified DNA is then digested with restriction enzymes Nco I and Sma I and fractionated on an agarose gel. The appropriate band can be isolated from the gel and combined with a 4.9 kb Nco I-Sma I fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb Sal I-Nco I promoter fragment of the maize 27 kD zein gene and a 0.96 kb Sma I-Sal I fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform E. coli XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when subcultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Frommn et al., (1990) *Bio/Technology* 8:833–839).

Example 8

Expression of Chimeric Genes in Dicot Cells

A seed-specific expression cassette composed of the promoter and trncription terminator from the gene encoding the P subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translatioe initiation codon about 1650 nucleotides downstream (3') from the translation stop codon of phaseolin. Between the 5' and 3' regions are the unique restriction endonuclease sites Nco I (which includes the ATO translation initiation codon), Sma I, Kpn I and Xba I. The entire cassette is flanked by Hind Ill sites.

The cDNA fragment of this gene may be generated by polymerase chain reaction (P)CR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pVC 1 8 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium. Soybean embryogenic suspension cultures may then be transformed by the method of particle gun bombardment (Klein et al. (1987) Nature (London) 32 7:70, U.S. Pat. No. 4,945,050). A DuPont BiolisticT™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/nL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 9

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One jig of protein from the soluble fraction of the culture can be separated by SDS-polyacrylamide gel electrophoresis. Gels can be observed for protein bands migrating at the expected molecular weight.

Example 10

Expression of Chimeric Genes in Insect Cells

The cDNAs encoding the instant polypeptides may be introduced into the baculovirus genome itself. For this purpose the cDNAs may be placed under the control of the polyhedron promoter, the IE1 promoter, or any other one of the baculovirus promoters. The DNA, together with appropriate leader sequences is then inserted into a baculovirus transfer vector using standard molecular cloning techniques. Following transformation of *E. coil* DH5α, isolated colonies are chosen and plasmid DNA is prepared and is analyzed by restriction enzyme analysis. Colonies containing the appropriate fragment are isolated, propagated, and plasmid DNA is prepared for cotransfection.

*Spodoptera frugiperda* cells (Sf-9) are propagated in ExCell® 401 media (JRH Biosciences, Lenexa, Kans.) supplemented with 3.0% fetal bovine serum. Lipofectin® (50 μL at 0.1 mg/mL, Gibco/BRL) is added to a 50 μL aliquot of the transfer vector containing the PDI gene (500 ng) and linearized polyhedrin-negative AcNPV (2.5 μg, Baculogold® viral DNA, Pharmigen, San Diego, Calif.).

Sf-9 cells (approximate 50% monolayer) are co-transfected with the viral DNA/transfer vector solution. The supernatant fluid from the co-transfection experiment is collected at 5 days post-transfection and recombinant viruses are isolated employing standard plaque purification protocols, wherein only polyhedrin-positive plaques are selected (O'Reilly et al. (1992), *Baculovirus Expression Vectors: A Laboratory Manual*, W. H. Freeman and Company, New York.). Sf-9 cells in 35 mM petri dishes (50% monolayer) are inoculated with 100 μL of a serial dilution of the viral suspension, and supernatant fluids are collected at 5 days post infection. In order to prepare larger quantities of virus for characterization, these supernatant fluids are used to inoculate larger tissue cultures for large scale propagation of recombinant viruses. Expression of the instant polypeptides encoded by the recombinant baculovirus is confirmed by bioassay.

What is claimed is:

1. An isolated polynucleotide comprising:
   (a) a nucleic acid sequence encoding a polypeptide having protein disulfide isomerase activity, wherein the polypeptide has an amino acid sequence of at least 80% sequence identity based on Clustal method of alignment when compared to one of SEQ ID NO:16 or 18; or
   (b) a complement of the nucleic acid sequence wherein the complement and nucleic acid sequence consist of the same number of nucleotides and are 100% complementary.

2. A chimeric gene comprising the isolated polynucleotide of claim 1 operably linked to at least one regulatory sequence.

3. A host cell comprising the chimeric gene of claim 2.

4. An isolated host cell compromising an isolated polynucleotide of claim 1.

5. The isolated host cell of claim 4 wherein the isolated host is selected from the group consisting of plant, insect, yeast, bacteria, and virus.

6. A virus comprising the isolated polynucleotide of claim 1.

7. The polynucleotide of claim 1, wherein the amino acid sequence of the polypeptide and the amino acid sequence of SEQ ID NO:16 or 18 have at least 90% identity based on the Clustal alignment method.

8. The polynucleotide of claim 1, wherein the amino acid sequence of the polypeptide and the amino acid sequence of SEQ ID NO:16 or 18 have at least 95% identity based on the Clustal alignment method.

9. The polynucleotide of claim 1, wherein the nucleic acid sequence comprises the nucleotide sequence of SEQ ID NO:15 or 17.

10. The polynucleotide of claim 1, wherein the amino acid sequence of the polypeptide comprises the amino acid sequence of SEQ ID NO:16 or 18.

11. A vector comprising the polynucleotide of claim 1.

12. A method for transforming a cell comprising transforming a cell with the polynucleotide of claim 1.

13. A recombinant baculovirus comprising the polynucleotide of claim 1.

14. A method for producing a plant comprising transforming a plant cell with the polynucleotide of claim 1 and regenerating a plant from the transformed plant cell.

15. A method for enhancing the yield of a transgenic secreted protein by co-transforming a cell with a polynucleotide encoding a secreted polypeptide and a polynucleotide of claim 1.

16. A method for isolating a polypeptide encoded by the polynucleotide of claim 1 comprising isolating the polypeptide from a cell containing a chimeric gene comprising the polynucleotide operably linked to a regulatory sequence.

* * * * *

SEQUENCE LISTING

<160> NUMBER OF SEQ ID NOS: 32

<210> SEQ ID NO 1
<211> LENGTH: 2149
<212> TYPE: DNA
<213> ORGANISM: Argiope sp.

<400> SEQUENCE: 1

```
gctcgagttt tcctttctct tgcggcgttg gtgttttcag tgtcaagagt agcagttttc      60
atataccggc tttctattta acacggagca atgtttatta aattactaat aactacgcta     120
tgtattgcat ccactatcgc agatgaaatt aagaaagaaa atcatgtttt agttttgaca     180
aatgataatt tcgaaggtgc aatcaaagat aaaaacgttc tggtcgaatt ctatgctcca     240
tggtgtgggc attgtaaggc tcttgaaccc caatatgcca aagccgcaga gagtctagct     300
gaagaaaaat ctgaactact cttggctaaa gttgatgcca cagttgaaac tgatcttgct     360
gaacggtatg gagttcgtgg atacccaacc atcaaattct tccgtgaagg aaagatcttc     420
gaatataatg gaggacgaac ttcagatgaa attatcagat ggcttaaaaa gaaaactgga     480
cctcccgcag ttgatttatc atctgtagaa gatgccaaaa agtttgttga tagtaacgaa     540
gttgctgttg ttgggttttt caaggatctt gaaagtgcag atgcaaagat tttcaagagt     600
gttgcatcag aaatggatga cttcgtattc ggtattacag atgacgatgt tgtttattct     660
gaacttaagg cctcaaagga tggagtcatt cttttttaaaa agtttgatga aggacgaaat     720
gaatatgaag gtgaattgaa ggaagaggat ctgaaaaaat tcttgaaatc gaacagcttg     780
ccattagtag ttgaattcag ccatgaaaca gcacaaaaga tctttggcgg agacattaaa     840
gcacacaatc ttctgttcat cagtaaagaa tcttcagatt atgaaagccg tgtagatgtc     900
ttccgtaagg tagcaaagga attcaaaggc aaggttttgt ttgttacaat caataccgat     960
gatgaagatc atgaaaagat catggacttc tttggcttga agaaagaaga tactccaact    1020
atgagattga tcaagcttga agaagaaatg gctaaattca agcctcctac cgaaggaaac    1080
agcgaaagtg aaattagaga cttcgtaaat ggtgtttggg aaggaaagat aaagcaacat    1140
ttactttctg aagacattcc tgaaggatgg gataagaac ctgtaaaagt tcttgtagga    1200
aagaattttg atgaagtggc ttttgacaaa tccaagaatg ttcttgttga attctatgct    1260
ccatggtgtg gtcactgcaa gcagttggct cccatttatg atgagcttgg tgaaaagtac    1320
```

-continued

```
aaagacagag atgatgttgt tattgccaaa atggacgcta cagcaaatga attggaacat    1380
actaaaatca atagctatcc tactattaaa ttgtacaaaa aaggcacaaa tgaggttgtt    1440
gagtacaatg gagaacgtac tttagaaggc attaataaat tcactgaaac tgatggagaa    1500
tatggaaaag ctgctcccga tgaggaggaa gctgaagaag cagtcaggga gatgcgcag    1560 gcacatcgtg atgaactata agcatcgcaa cttaataggt cattcatttc atactcctca    1620
tacacgcatt gtgtaccaaa gtcaagcgca atcagttgtt aaactcattt ttccattcaa    1680
gccaatggct ggtctccagg ggttaaaata aatcggacat tttgtgttgt ggttgtgctg    1740
aacaaattgg atttaatgat actaataaaa aaaaaattgt tctgtaaaat atttttctta    1800
tcagatttgt tagagattat atacaaagca ggcattttaa gtttcaatta tttcattatt    1860
tttttatgct gatgttgtgt tcaaaaacgg tgtgaacaaa gatgttatgc tgttttata    1920 atttttttat ttaagtaaat gttaaatgat aacttttgaa gattttcat ttattacgtt    1980 atttaaatac atctgttcat acttttattt ttaatcaaat aattggcaat agaataaaat    2040
attttttata taaaaaacat agttcatttt gaattaaatg ctcgtcttcc ttgtgtgtat    2100
taatattaca ggtgtaataa aatacttgtt aaaaaaaaaa aaaaaaaa                 2149
```

<210> SEQ ID NO 2
<211> LENGTH: 496
<212> TYPE: PRT
<213> ORGANISM: Argiope sp.

<400> SEQUENCE: 2

```
Met Phe Ile Lys Leu Leu Ile Thr Thr Leu Cys Ile Ala Ser Thr Ile
  1               5                  10                  15

Ala Asp Glu Ile Lys Lys Glu Asn His Val Leu Val Leu Thr Asn Asp
                 20                  25                  30

Asn Phe Glu Gly Ala Ile Lys Asp Lys Asn Val Leu Val Glu Phe Tyr
             35                  40                  45

Ala Pro Trp Cys Gly His Cys Lys Ala Leu Glu Pro Gln Tyr Ala Lys
         50                  55                  60

Ala Ala Glu Ser Leu Ala Glu Glu Lys Ser Glu Leu Leu Leu Ala Lys
     65                  70                  75                  80

Val Asp Ala Thr Val Glu Thr Asp Leu Ala Glu Arg Tyr Gly Val Arg
                 85                  90                  95

Gly Tyr Pro Thr Ile Lys Phe Phe Arg Glu Gly Lys Ile Phe Glu Tyr
            100                 105                 110

Asn Gly Gly Arg Thr Ser Asp Glu Ile Ile Arg Trp Leu Lys Lys Lys
        115                 120                 125

Thr Gly Pro Pro Ala Val Asp Leu Ser Ser Val Glu Asp Ala Lys Lys
    130                 135                 140

Phe Val Asp Ser Asn Glu Val Ala Val Gly Phe Phe Lys Asp Leu
145                 150                 155                 160

Glu Ser Ala Asp Ala Lys Ile Phe Lys Ser Val Ala Ser Glu Met Asp
                165                 170                 175

Asp Phe Val Phe Gly Ile Thr Asp Asp Val Val Tyr Ser Glu Leu
            180                 185                 190

Lys Ala Ser Lys Asp Gly Val Ile Leu Phe Lys Phe Asp Glu Gly
        195                 200                 205

Arg Asn Glu Tyr Glu Gly Glu Leu Lys Glu Asp Leu Lys Lys Phe
    210                 215                 220

Leu Lys Ser Asn Ser Leu Pro Leu Val Val Glu Phe Ser His Glu Thr
```

```
                225                 230                 235                 240
Ala Gln Lys Ile Phe Gly Gly Asp Ile Lys Ala His Asn Leu Leu Phe
                245                 250                 255
Ile Ser Lys Glu Ser Ser Asp Tyr Glu Ser Arg Val Asp Val Phe Arg
                260                 265                 270
Lys Val Ala Lys Glu Phe Lys Gly Lys Val Leu Phe Val Thr Ile Asn
                275                 280                 285
Thr Asp Asp Glu Asp His Glu Lys Ile Met Asp Phe Phe Gly Leu Lys
                290                 295                 300
Lys Glu Asp Thr Pro Thr Met Arg Leu Ile Lys Leu Glu Glu Glu Met
305                 310                 315                 320
Ala Lys Phe Lys Pro Pro Thr Glu Gly Asn Ser Glu Ser Glu Ile Arg
                325                 330                 335
Asp Phe Val Asn Gly Val Leu Glu Gly Lys Ile Lys Gln His Leu Leu
                340                 345                 350
Ser Glu Asp Ile Pro Glu Gly Trp Asp Lys Glu Pro Val Lys Val Leu
                355                 360                 365
Val Gly Lys Asn Phe Asp Glu Val Ala Phe Asp Lys Ser Lys Asn Val
                370                 375                 380
Leu Val Glu Phe Tyr Ala Pro Trp Cys Gly His Cys Lys Gln Leu Ala
385                 390                 395                 400
Pro Ile Tyr Asp Glu Leu Gly Glu Lys Tyr Lys Asp Arg Asp Asp Val
                405                 410                 415
Val Ile Ala Lys Met Asp Ala Thr Ala Asn Glu Leu Glu His Thr Lys
                420                 425                 430
Ile Asn Ser Tyr Pro Thr Ile Lys Leu Tyr Lys Lys Gly Thr Asn Glu
                435                 440                 445
Val Val Glu Tyr Asn Gly Glu Arg Thr Leu Glu Gly Ile Asn Lys Phe
450                 455                 460
Thr Glu Thr Asp Gly Glu Tyr Gly Lys Ala Ala Pro Asp Glu Glu Glu
465                 470                 475                 480
Ala Glu Glu Ala Val Arg Glu Asp Ala Gln Ala His Arg Asp Glu Leu
                485                 490                 495

<210> SEQ ID NO 3
<211> LENGTH: 1843
<212> TYPE: DNA
<213> ORGANISM: Scolopendra canidens DS

<400> SEQUENCE: 3
gcacgagtat aaacgcctgc ctctccgttt gcttctgctt gccacgtttg acttttcctc     60
taaccagcgg cattggtgca tgtttagtgt caggtgatag gcttttcatt taccggcttg    120
aacttaaatt tataaaatgt atataaagct tcttattctt agtttatgca tatatttatg    180
tatagctgat gaaattaaaa agaaaagtc agttttagtg ttgaccaaag acaattttga    240
aggagcaatc aaagataaaa gtgtactcgt cgagttttat gctccttggt gtggtcattg    300
taaggcccta gaacctgaat atgctaaagc cgctcagatc ttggaagagg aaaagtccga    360
cttactgttg gctaaagttg atgctacagc ggaaactgat ttagctgaac agcatggcgt    420
tcgtgggtat ccaactatta gttttttccg agagggtaaa gtgatagaat actctggtgg    480
acgaactgct gatgacatta tacgctggct gaaaaagaag actgggcctc cagcaactga    540
tttaactaca gtagaggcaa caaaatcttt tattgatggt ggtgaggtag tagttgtagg    600
cttctttaaa gaccaaaatt cagatcaggc aaagattttc aagaatgttg ctgcagaaat    660
```

```
ggatgacttt gttttcggca ttacttcaac tgatgaggtg tacaatgaat taaaggctac    720
acaagatggc gttgttttgt ttaaaaagtt tgatgaagga aggaatgttt atgaaggtga    780
attatcagaa gaaaaattga aaaaattctt gaaatctaat agcctgcctc tagttgttga    840
gtttacccat gaatcagctc agaaaatctt tggggtgac attaaagccc ataatttact     900
cttcatcagc aaaggaacct cggattatga agcaaaatt gaagccttcc gtaaagtcgc     960
taaagaattc aaaggcaaag ttcttttttgt tactatcgat actgatgatg aagatcatga  1020
gagaatcatg gaattctttg gtcttaaaaa agaagaggcg cctaccatga gactgatcaa   1080
actagaagat gaaatgacta aattcaaacc tactactaca ggaattgagg aaagtgatat   1140
tagaggattt gttactggtg ttttagaagg aaagataaag caacacttgc tttctgaaga   1200
tgttcctgaa ggatgggata agagcctgt gaaaattcta gttggaaaaa attttgatga    1260
agtagtattt gataaaacaa agaatgttct agttgaattt tatgctccat ggtgtggcca   1320
ttgtaaacag ctagctccta tttatgatga attgggtgag aaatacaagg atcaagctga   1380
tattgtaatt gctaagatgg atgctactgc aaatgaattg gagcatacca agattaacag   1440
ttttcccaca atcaagttgt acaaaaaaga tacaaatgaa gtggttgatt tcaatggaga   1500
acgcacactt gaaggaatta gcaggtttat tgatactggt ggtgttgatg gggcagctgt   1560
taaagaagag gaggaagatg aggaagaaga aaaagatgac gaacaggcca agcgtgatga   1620
gctttaaagg cattatcaca agacttaagt catcatctcc attttctca tacaacattg    1680 tgtaccaaag ttgagtgcga tcagttcttg taaccattaa tttcattcat gccaatggct   1740
ggattccagg ggttgtaaca aattaaggac cttttctttg ttcagtgaat gtgccgaagc   1800
agttctaata aatatttgt tttttaaaaa aaaaaaaaaa aaa                       1843
```

<210> SEQ ID NO 4
<211> LENGTH: 496
<212> TYPE: PRT
<213> ORGANISM: Scolopendra canidens DS

<400> SEQUENCE: 4

```
Met Tyr Ile Lys Leu Leu Ile Leu Ser Leu Cys Ile Tyr Leu Cys Ile
  1               5                  10                  15

Ala Asp Glu Ile Lys Lys Glu Lys Ser Val Leu Val Leu Thr Lys Asp
             20                  25                  30

Asn Phe Glu Gly Ala Ile Lys Asp Lys Ser Val Leu Val Glu Phe Tyr
         35                  40                  45

Ala Pro Trp Cys Gly His Cys Lys Ala Leu Glu Pro Glu Tyr Ala Lys
     50                  55                  60

Ala Ala Gln Ile Leu Glu Glu Lys Ser Asp Leu Leu Ala Lys
 65                  70                  75                  80

Val Asp Ala Thr Ala Glu Thr Asp Leu Ala Glu Gln His Gly Val Arg
                 85                  90                  95

Gly Tyr Pro Thr Ile Lys Phe Arg Glu Gly Lys Val Ile Glu Tyr
            100                 105                 110

Ser Gly Gly Arg Thr Ala Asp Asp Ile Ile Arg Trp Leu Lys Lys Lys
        115                 120                 125

Thr Gly Pro Pro Ala Thr Asp Leu Thr Thr Val Glu Ala Thr Lys Ser
    130                 135                 140

Phe Ile Asp Gly Gly Glu Val Val Val Gly Phe Phe Lys Asp Gln
145                 150                 155                 160
```

```
Asn Ser Asp Gln Ala Lys Ile Phe Lys Asn Val Ala Ala Glu Met Asp
            165                 170                 175

Asp Phe Val Phe Gly Ile Thr Ser Thr Asp Glu Val Tyr Asn Glu Leu
            180                 185                 190

Lys Ala Thr Gln Asp Gly Val Val Leu Phe Lys Lys Phe Asp Glu Gly
            195                 200             205

Arg Asn Val Tyr Glu Gly Glu Leu Ser Glu Lys Leu Lys Lys Phe
    210                 215                 220

Leu Lys Ser Asn Ser Leu Pro Leu Val Val Glu Phe Thr His Glu Ser
225                 230                 235                 240

Ala Gln Lys Ile Phe Gly Gly Asp Ile Lys Ala His Asn Leu Leu Phe
                245                 250                 255

Ile Ser Lys Gly Thr Ser Asp Tyr Glu Ser Lys Ile Glu Ala Phe Arg
            260                 265                 270

Lys Val Ala Lys Glu Phe Lys Gly Lys Val Leu Phe Val Thr Ile Asp
            275                 280                 285

Thr Asp Asp Glu Asp His Glu Arg Ile Met Glu Phe Phe Gly Leu Lys
    290                 295                 300

Lys Glu Glu Ala Pro Thr Met Arg Leu Ile Lys Leu Glu Asp Glu Met
305                 310                 315                 320

Thr Lys Phe Lys Pro Thr Thr Thr Gly Ile Glu Ser Asp Ile Arg
            325                 330                 335

Gly Phe Val Thr Gly Val Leu Glu Gly Lys Ile Lys Gln His Leu Leu
            340                 345                 350

Ser Glu Asp Val Pro Glu Gly Trp Asp Lys Glu Pro Val Lys Ile Leu
            355                 360                 365

Val Gly Lys Asn Phe Asp Glu Val Val Phe Asp Lys Thr Lys Asn Val
    370                 375                 380

Leu Val Glu Phe Tyr Ala Pro Trp Cys Gly His Cys Lys Gln Leu Ala
385                 390                 395                 400

Pro Ile Tyr Asp Glu Leu Gly Glu Lys Tyr Lys Asp Gln Ala Asp Ile
            405                 410                 415

Val Ile Ala Lys Met Asp Ala Thr Ala Asn Glu Leu Glu His Thr Lys
            420                 425                 430

Ile Asn Ser Phe Pro Thr Ile Lys Leu Tyr Lys Lys Asp Thr Asn Glu
            435                 440                 445

Val Val Asp Phe Asn Gly Glu Arg Thr Leu Glu Gly Ile Ser Arg Phe
    450                 455                 460

Ile Asp Thr Gly Gly Val Asp Gly Ala Ala Val Lys Glu Glu Glu Glu
465                 470                 475                 480

Asp Glu Glu Glu Glu Lys Asp Asp Glu Gln Ala Lys Arg Asp Glu Leu
                485                 490                 495
```

<210> SEQ ID NO 5
<211> LENGTH: 497
<212> TYPE: DNA
<213> ORGANISM: Heliothus virescens]
<220> FEATURE:
<221> NAME/KEY: unsure
<222> LOCATION: (452)

<400> SEQUENCE: 5

```
gtttcgtctt cggagcaggc ttgtgaagtg ccgtattttc caacatgaga gtgatcctat    60
ttacggcgtt agcccttctg ggcaccgctt tggccgatga agtacccact gaagaaaacg   120
tactcgtttt aagcaaatct aacttcgaag gagtcatttc agcaaacaac ttcatattag   180
```

-continued

```
tggaattcta tgcgccatgg tgcggtcact gcaagtccct cgctccggag tacgccaagg    240
ccgccaccaa gctggccgag gaggagtctc ccatcaaact ggccaaggtt gatgccacgc    300
aagagcaaga gctcgctgag agctacggcg tcagggata cccgaccctc aagttcttca     360
gaaacggcag ccctattgat tacactggtg gtcgccaagc tgacgacatt gtctcctggc    420
tgaagaagaa gactggtcct cccgcccttg angtgcctc tgctgagca agccaaggaa      480 ctcaattgcc gccaaca                                                    497
```

<210> SEQ ID NO 6
<211> LENGTH: 133
<212> TYPE: PRT
<213> ORGANISM: Heliothus virescens]

<400> SEQUENCE: 6

```
Met Arg Val Ile Leu Phe Thr Ala Leu Ala Leu Leu Gly Thr Ala Leu
  1               5                  10                  15

Ala Asp Glu Val Pro Thr Glu Glu Asn Val Leu Val Leu Ser Lys Ser
             20                  25                  30

Asn Phe Glu Gly Val Ile Ser Ala Asn Asn Phe Ile Leu Val Glu Phe
         35                  40                  45

Tyr Ala Pro Trp Cys Gly His Cys Lys Ser Leu Ala Pro Glu Tyr Ala
     50                  55                  60

Lys Ala Ala Thr Lys Leu Ala Glu Glu Ser Pro Ile Lys Leu Ala
 65                  70                  75                  80

Lys Val Asp Ala Thr Gln Glu Gln Glu Leu Ala Glu Ser Tyr Gly Val
                 85                  90                  95

Arg Gly Tyr Pro Thr Leu Lys Phe Phe Arg Asn Gly Ser Pro Ile Asp
            100                 105                 110

Tyr Thr Gly Gly Arg Gln Ala Asp Asp Ile Val Ser Trp Leu Lys Lys
        115                 120                 125

Lys Thr Gly Pro Pro
    130
```

<210> SEQ ID NO 7
<211> LENGTH: 1859
<212> TYPE: DNA
<213> ORGANISM: Vaejovis carolinianus

<400> SEQUENCE: 7

```
gcacgagttt tagtagaaaa atgttgggtg cggttacttt atctacaatt ttactagttg    60
ttatagcagc agcagatgaa atcaagaaag acggcgaagt tctagtttta aacaaagaca   120
atttccaaaa agctattcaa gaaacaaac atatcttggt tgaattttat gcaccatggt    180
gtggccactg taaagcactt gagccagaat atgccaaagc agccaagcag cttaaagaag   240
aacagtctga tattgctctt ggtaagattg atgccacagc agagagtgag ttagcggaag   300
agtatgatgt ccgaggatat cctacaataa aattcatcag ggatggcaaa ccttcagagt   360
acaaaggtgg tcgaacagcg gaagatattg ttcgctggct gaagaagaaa gttggtcctc   420
cagctgaaaa tcttgacaca gttgacagtg tcaaaacatt ccaatcaagt gcagaagttg   480
tattagttgg tttctttaaa gatcaatcat cagataaagc taaggtgttc ttggaggtag   540
ctttagaatc tgatgactat gcttttgaa tcacatcaca ggatgatgtg tttaaggcat    600
ataatgtgga aaaagatgga attgttttgt taaacagtt tgatgaagga agaaatgact   660
ttgaaggaga ataacagca gatgctttaa aagagtttat taatgctaac agcttgccat    720
```

```
tggttgttga gttcaatcaa gatactgcac agaaagtctt tggtggtgaa atcaaagctc    780
acaatttact ttttgtcagc aaacagcaga gtgaagagta tgagaaatta cttgaagtct    840
tccgtaaagt tgccaaagat tttaagaata aggtattgtt tgttacaatt gacatagatg    900
aagaggacca tgaaagaata atggaatttt ttggaatgaa gaagaagat gcaccagata     960 tgcgtttgat cagattagaa gaggagatga caaagtttaa accaccatct cctggactct   1020
cagaagaaaa tatacgctct tttgttcagg gagttttaga tggaaaaatc aagaggcact   1080
tgctgtctga aagtgttcca gatgactggg acaagggagc agttaaggtt ctggttggac   1140
aaaacttcga tgatgttgca tttgacaaat caaaagatgt gcttgttgag ttttatgcac   1200
cttggtgtgg acattgcaaa cagcttgcac ccatctatga agaacttgga gagaagtaca   1260
aagatcagtc atctattgtt attgcaaaaa tggatgccac taccaatgaa ctggaccatg   1320
taaaaatcca tagttttccc acaattaaat tattcaaaaa agataccaat gaggtcatag   1380
acttcaatgg tgaacgcaca cttgaaggac tgacaaaatt tattgattca ggaggagtgg   1440
atggcgcttc accaaaggaa gaggagattg acgaagagga ggaaaaggat gatgatgaaa   1500
agaaaaggga cgaactgtga ttttcactg aaaactaatt tacacatgtt gcttcattgc    1560
agcagatttt gtccattcct gaattttcct gtgtacagaa aaggttgtgt tgaacaatag   1620
gttttggcaa catttaacgt aacaaacaag gcttgctaag tattgccatt tatcaaatgt   1680
taaaatgcca aagcatattt gtaggaagtc tttttaattt aaaatatttt tcccctaact   1740
ttttattttt tatctttat taaaatgaat gacttttaaa tcatcggtgg tgcaaatgct    1800
ggtcgtggaa attatttgga atgctaaaac aaagcaaaac aaattgcgat ggtcgtact    1859

<210> SEQ ID NO 8
<211> LENGTH: 499
<212> TYPE: PRT
<213> ORGANISM: Vaejovis carolinianus

<400> SEQUENCE: 8

Met Leu Gly Ala Val Thr Leu Ser Thr Ile Leu Leu Val Val Ile Ala
 1               5                  10                  15

Ala Ala Asp Glu Ile Lys Lys Asp Gly Glu Val Leu Val Leu Asn Lys
                20                  25                  30

Asp Asn Phe Gln Lys Ala Ile Gln Glu Asn Lys His Ile Leu Val Glu
            35                  40                  45

Phe Tyr Ala Pro Trp Cys Gly His Cys Lys Ala Leu Glu Pro Glu Tyr
        50                  55                  60

Ala Lys Ala Ala Lys Gln Leu Lys Glu Glu Gln Ser Asp Ile Ala Leu
    65                  70                  75                  80

Gly Lys Ile Asp Ala Thr Ala Glu Ser Glu Leu Ala Glu Glu Tyr Asp
                85                  90                  95

Val Arg Gly Tyr Pro Thr Ile Lys Phe Ile Arg Asp Gly Lys Pro Ser
            100                 105                 110

Glu Tyr Lys Gly Gly Arg Thr Ala Glu Asp Ile Val Arg Trp Leu Lys
        115                 120                 125

Lys Lys Val Gly Pro Pro Ala Glu Asn Leu Asp Thr Val Asp Ser Val
    130                 135                 140

Lys Thr Phe Gln Ser Ser Ala Glu Val Val Leu Val Gly Phe Phe Lys
145                 150                 155                 160

Asp Gln Ser Ser Asp Lys Ala Lys Val Phe Leu Glu Val Ala Leu Glu
                165                 170                 175
```

Ser Asp Asp Tyr Ala Phe Gly Ile Thr Ser Gln Asp Val Phe Lys
            180                 185                 190
Ala Tyr Asn Val Glu Lys Asp Gly Ile Val Leu Phe Lys Gln Phe Asp
            195                 200                 205
Glu Gly Arg Asn Asp Phe Glu Gly Glu Ile Thr Ala Asp Ala Leu Lys
            210                 215                 220
Glu Phe Ile Asn Ala Asn Ser Leu Pro Leu Val Val Glu Phe Asn Gln
225                 230                 235                 240
Asp Thr Ala Gln Lys Val Phe Gly Gly Glu Ile Lys Ala His Asn Leu
            245                 250                 255
Leu Phe Val Ser Lys Gln Gln Ser Glu Glu Tyr Glu Lys Leu Leu Glu
            260                 265                 270
Val Phe Arg Lys Val Ala Lys Asp Phe Lys Asn Lys Val Leu Phe Val
            275                 280                 285
Thr Ile Asp Ile Asp Glu Glu Asp His Glu Arg Ile Met Glu Phe Phe
            290                 295                 300
Gly Met Lys Lys Glu Asp Ala Pro Asp Met Arg Leu Ile Arg Leu Glu
305                 310                 315                 320
Glu Glu Met Thr Lys Phe Lys Pro Pro Ser Pro Gly Leu Ser Glu Glu
            325                 330                 335
Asn Ile Arg Ser Phe Val Gln Gly Val Leu Asp Gly Lys Ile Lys Arg
            340                 345                 350
His Leu Leu Ser Glu Ser Val Pro Asp Asp Trp Asp Lys Gly Ala Val
            355                 360                 365
Lys Val Leu Val Gly Gln Asn Phe Asp Val Ala Phe Asp Lys Ser
            370                 375                 380
Lys Asp Val Leu Val Glu Phe Tyr Ala Pro Trp Cys Gly His Cys Lys
385                 390                 395                 400
Gln Leu Ala Pro Ile Tyr Glu Glu Leu Gly Glu Lys Tyr Lys Asp Gln
            405                 410                 415
Ser Ser Ile Val Ile Ala Lys Met Asp Ala Thr Thr Asn Glu Leu Asp
            420                 425                 430
His Val Lys Ile His Ser Phe Pro Thr Ile Lys Leu Phe Lys Lys Asp
            435                 440                 445
Thr Asn Glu Val Ile Asp Phe Asn Gly Glu Arg Thr Leu Glu Gly Leu
            450                 455                 460
Thr Lys Phe Ile Asp Ser Gly Val Asp Gly Ala Ser Pro Lys Glu
465                 470                 475                 480
Glu Glu Ile Asp Glu Glu Glu Lys Asp Asp Asp Glu Lys Lys Arg
            485                 490                 495
Asp Glu Leu

<210> SEQ ID NO 9
<211> LENGTH: 2170
<212> TYPE: DNA
<213> ORGANISM: Argiope sp.

<400> SEQUENCE: 9
gcacgagaaa aagtataagc atcagtgaac cgctgaagtc tattgatttt taccaaaaga      60
tttacaatga agctgttatt tctgtcatca atacttagtt gtacattatc tgtaatactt     120
tgtagtgatg tcctagattt ttccggtgcc gatttcgaag atcgaatagc agaacatgat     180
gcaattttag ttgaattctt cgctccttgg tgtggacatt gtaagagatt agcacctgaa     240

-continued

```
tatgacaaag catctacgat attaaaaaaa gctgacccac ctataccact agcaaaggtt    300
gactgcacat cagataatgg taaagataca tgttcaaaat atggtgtaag tggttatcct    360
actttaaaga tatttagagg tggagaattt tcttcagaat ataatggtcc tcgtgatgca    420
gatggtattg ttaagtatat gaaggctcaa gttggtccaa gttcaaaaga acttcaatct    480
ttggaagatg cagagaaaat tttaaaagat gatattgttg tgattggtta ctttgctgat    540
tcgtcaaata aattaaagga agaattctta aaagcagctg ataaactcag agaatctgta    600
tcttttgcac atacatctag taaagacatt ttagacaaat atgggtattc tgatgaaatt    660
gttttatacc gtcccaagat cttctggagt aaatttgaac cccaagaaat aaaatataca    720
ggtgatgcag ataaaggaga gatttctcaa tttattaaag acaactacca tggtcttgtt    780
ggtcatagaa cacatgacaa tcacgatgac tttaaggctc ctcttattgt tgtatattat    840
gatgtagact atgtaaagaa tgtaaaaggc acaaactact ggcgtaacag agtaatgaag    900
gttgcacaga actacaaggg acaagtcaac tttgctatta gtaacaaaga caaatttttct   960 gctgaagttg aagattttgg tttaaaagct acaggagata aacctgtagt tgctgccaga   1020
aatgataaaa accagaaatt taatatgaag gaagaattca gtgttgaaaa ttttgaaact   1080
tttgtgaaaa aattttttgga tggcagttta gaaccacact tgaaatctga acctgttcct   1140
gaaaagaacg acgggcctgt taaagtagct gttgcccaaa actttgaaga acttgtaatg   1200
gaaaatgaca aagatgtatt gatcgaattt tatgcccat ggtgtggaca ttgtaagaaa    1260
ttggctccta cttatgaaga acttggtcaa agttggaag gtgaagatgt agagattgtg    1320
aaaatggatg ctacagctaa tgatgttcca cctacatttg aggttcatgg attcccaaca   1380
ttatattggg tacctaaaac acacaagtct agtccgaaga aatatgaagg tggccgagaa   1440
atcaaggact ttatcaatta cattgccaag catgctacaa atgaattgaa acaatatgac   1500
cgatctggca aaagaagtc caaggaagag ctataagtta atatcactct tttaggaact   1560 attttcaat gtgcatagtt tgtgttaagc atcaatcatg ttaatcttgt tacatattaa   1620
ttgaacaaat gtggtaggc atgtactgat catctgttca tacgttccaa attgactctg   1680
tgggacctaa agtgtctttt tgtaataaaa cgttttttta tactttctgct gttttttttc    1740 cccttacgag tggaattttt ttactttta ctttttattct ttattaatgg gtattgagtc   1800
tgaaattatt tatttagtct tttattaatc ttttccttgt tattttaaga ttgaatatct   1860
actaaacatt ttctttaaaa aaatctatgc aatttgtaat atgccatcat gaatttcatg   1920
gaagttcttg tatattcatt agatcaatca aaatatattt gcagtgcaga tatttaaagc   1980
tgaacaattt cttcgtagag taatacacat gtatttaaaa tgatctgcaa aagccttaac   2040
tttgaatgtt acttgtacat ttgttgcaaa atagcatttg tcgtattta tgtaatttt     2100 ctatttaaat cgattgaaat aaaggtagtt cttttaaaaa aaaaaaaaaa aaaaaaaaa    2160 aaaaaaaaaa                                                          2170
```

<210> SEQ ID NO 10
<211> LENGTH: 489
<212> TYPE: PRT
<213> ORGANISM: Argiope sp.

<400> SEQUENCE: 10

```
Met Lys Leu Leu Phe Leu Ser Ser Ile Leu Ser Cys Thr Leu Ser Val
 1               5                  10                  15

Ile Leu Cys Ser Asp Val Leu Asp Phe Ser Gly Ala Asp Phe Glu Asp
            20                  25                  30
```

```
Arg Ile Ala Glu His Asp Ala Ile Leu Val Glu Phe Phe Ala Pro Trp
        35                  40                  45
Cys Gly His Cys Lys Arg Leu Ala Pro Glu Tyr Asp Lys Ala Ser Thr
    50                  55                  60
Ile Leu Lys Lys Ala Asp Pro Pro Ile Pro Leu Ala Lys Val Asp Cys
65                  70                  75                  80
Thr Ser Asp Asn Gly Lys Asp Thr Cys Ser Lys Tyr Gly Val Ser Gly
                85                  90                  95
Tyr Pro Thr Leu Lys Ile Phe Arg Gly Gly Glu Phe Ser Ser Glu Tyr
            100                 105                 110
Asn Gly Pro Arg Asp Ala Asp Gly Ile Val Lys Tyr Met Lys Ala Gln
            115                 120                 125
Val Gly Pro Ser Ser Lys Glu Leu Gln Ser Leu Glu Asp Ala Glu Lys
        130                 135                 140
Ile Leu Lys Asp Asp Ile Val Ile Gly Tyr Phe Ala Asp Ser Ser
145                 150                 155                 160
Asn Lys Leu Lys Glu Glu Phe Leu Lys Ala Ala Asp Lys Leu Arg Glu
                165                 170                 175
Ser Val Ser Phe Ala His Thr Ser Ser Lys Asp Ile Leu Asp Lys Tyr
            180                 185                 190
Gly Tyr Ser Asp Glu Ile Val Leu Tyr Arg Pro Lys Ile Phe Trp Ser
            195                 200                 205
Lys Phe Glu Pro Gln Glu Ile Lys Tyr Thr Gly Asp Ala Asp Lys Gly
        210                 215                 220
Glu Ile Ser Gln Phe Ile Lys Asp Asn Tyr His Gly Leu Val Gly His
225                 230                 235                 240
Arg Thr His Asp Asn His Asp Asp Phe Lys Ala Pro Leu Ile Val Val
                245                 250                 255
Tyr Tyr Asp Val Asp Tyr Val Lys Asn Val Lys Gly Thr Asn Tyr Trp
            260                 265                 270
Arg Asn Arg Val Met Lys Val Ala Gln Asn Tyr Lys Gly Gln Val Asn
            275                 280                 285
Phe Ala Ile Ser Asn Lys Asp Lys Phe Ser Ala Glu Val Glu Asp Phe
        290                 295                 300
Gly Leu Lys Ala Thr Gly Asp Lys Pro Val Val Ala Ala Arg Asn Asp
305                 310                 315                 320
Lys Asn Gln Lys Phe Asn Met Lys Glu Glu Phe Ser Val Glu Asn Phe
                325                 330                 335
Glu Thr Phe Val Lys Lys Phe Leu Asp Gly Ser Leu Glu Pro His Leu
            340                 345                 350
Lys Ser Glu Pro Val Pro Glu Lys Asn Asp Gly Pro Val Lys Val Ala
            355                 360                 365
Val Ala Gln Asn Phe Glu Glu Leu Val Met Glu Asn Asp Lys Asp Val
        370                 375                 380
Leu Ile Glu Phe Tyr Ala Pro Trp Cys Gly His Cys Lys Lys Leu Ala
385                 390                 395                 400
Pro Thr Tyr Glu Glu Leu Gly Gln Lys Leu Glu Gly Glu Asp Val Glu
                405                 410                 415
Ile Val Lys Met Asp Ala Thr Ala Asn Asp Val Pro Pro Thr Phe Glu
            420                 425                 430
Val His Gly Phe Pro Thr Leu Tyr Trp Val Pro Lys Thr His Lys Ser
            435                 440                 445
```

Ser Pro Lys Lys Tyr Glu Gly Gly Arg Glu Ile Lys Asp Phe Ile Asn
    450                 455                 460

Tyr Ile Ala Lys His Ala Thr Asn Glu Leu Lys Gln Tyr Asp Arg Ser
465                 470                 475                 480

Gly Lys Lys Lys Ser Lys Glu Glu Leu
                485

<210> SEQ ID NO 11
<211> LENGTH: 1584
<212> TYPE: DNA
<213> ORGANISM: Hottentotta judiaca

<400> SEQUENCE: 11

| | | | | | |
|---|---|---|---|---|---|
| gcacgagact | tggtccaaaa | tatgaagagg | cagcaacaat | tttgaagaaa | aatgatccac | 60 |
| ctgttccttt | agctaaggtg | gattgtacat | ctgatgctgg | aaaagaaact | tgttcaaaat | 120 |
| atggtgtcag | tggctatcct | actctcaaga | ttttccgaaa | tggtgaattt | tcttcagagt | 180 |
| acagtggtgg | gcgagaaaca | gatgctattg | taaaatatat | gaaatctcaa | gttggaccaa | 240 |
| gctctgtaga | aattaaaaca | cctgctgatg | ctaaaaagtt | attaagcaga | atcgaagtag | 300 |
| ttataattgg | attttttaag | gatgaaaaaa | gtcagttgaa | agaagaattt | ttaaaagttg | 360 |
| cagataaaat | gagagagacc | acttcctttg | gacacacatc | taatcaagaa | gttcttgatt | 420 |
| tatatggata | taaagatcaa | atagtgctct | tccgtcctca | gcatcttcaa | agcaaatttg | 480 |
| aagaaaagaa | attaaaatat | gaaggtggtc | tgaaaaatc | aaaaatagaa | gatttcatta | 540 |
| gagaaaatta | tcatggattg | gttggtcatc | gaactagtga | taatttccaa | gatttcaaga | 600 |
| atcctcttgt | tgtagcatat | tatgatgtag | actatgtaaa | aatactaaa | ggtacaaatt | 660 |
| attggcgtaa | tcgtatcatg | aaagtagcac | aacatttcaa | agacaaattg | aactttgctg | 720 |
| tatctaatat | aaatcaattt | tctgctgaaa | ttgaagaatt | tggcctaact | gttaaaggtg | 780 |
| ataagcctgc | aattgcagta | cgtaatgaaa | agcaacagaa | attccgaatg | actgatgaat | 840 |
| ttagcatgga | tgcatttgag | aaatttctta | aggactttt | agatgaaaag | ttagaagcac | 900 |
| acgtaaaatc | tgaaccaatt | ccagaaaata | atgatggacc | agttaaggtt | gcagttgcat | 960 |
| caaattttga | tgatattgta | acaaataatg | ataaagacat | cttgctagaa | ttttatgctc | 1020 |
| catggtgtgg | acattgtaaa | aaacttgctc | caacatatga | agaattaggc | acagagatga | 1080 |
| aacaggaaga | tgttgaaata | gttaaaatgg | atgcaacagc | aaatgatgtt | cctccaccct | 1140 |
| atgaagttca | tgggtttcca | acactttatt | gggttccaaa | aaatagcaaa | aataatccca | 1200 |
| aaaaatatga | tggtggtcga | gaattggatg | atttaataaa | atatatatct | aaacacgcca | 1260 |
| caaatgaatt | gaaaggatgg | gacaggaagg | gcactaaaaa | gtctgagaag | acagagctct | 1320 |
| gagctgttct | gtctaaattt | ttcacagttg | ttagtgataa | attcattttt | gtgatgtcca | 1380 |
| aaattcattt | gattttagt | ttacttggga | cttcatccac | tgactatcat | tcctgcagtt | 1440 |
| tgtcattaat | agcaactggg | ggggttggat | taagtgtaat | gtttaatgaa | tatttgtgaa | 1500 |
| ttttgaaggt | aaatgttaaa | taaatgtcaa | ttttgtttac | aaaaaaaaa | aaaaaaaaa | 1560 |
| aaaaaaaaa | aaaaaaaaaa | aaaa | | | | 1584 |

<210> SEQ ID NO 12
<211> LENGTH: 439
<212> TYPE: PRT
<213> ORGANISM: Hottentotta judiaca

<400> SEQUENCE: 12

```
Thr Arg Leu Gly Pro Lys Tyr Glu Ala Ala Thr Ile Leu Lys Lys
 1               5                  10                  15

Asn Asp Pro Pro Val Pro Leu Ala Lys Val Asp Cys Thr Ser Asp Ala
                 20                  25                  30

Gly Lys Glu Thr Cys Ser Lys Tyr Gly Val Ser Gly Tyr Pro Thr Leu
             35                  40                  45

Lys Ile Phe Arg Asn Gly Glu Phe Ser Ser Glu Tyr Ser Gly Gly Arg
 50                  55                  60

Glu Thr Asp Ala Ile Val Lys Tyr Met Lys Ser Gln Val Gly Pro Ser
 65                  70                  75                  80

Ser Val Glu Ile Lys Thr Pro Ala Asp Ala Lys Lys Leu Leu Ser Arg
                 85                  90                  95

Ile Glu Val Val Ile Ile Gly Phe Phe Lys Asp Glu Lys Ser Gln Leu
                100                 105                 110

Lys Glu Glu Phe Leu Lys Val Ala Asp Lys Met Arg Glu Thr Thr Ser
             115                 120                 125

Phe Gly His Thr Ser Asn Gln Glu Val Leu Asp Leu Tyr Gly Tyr Lys
130                 135                 140

Asp Gln Ile Val Leu Phe Arg Pro Gln His Leu Gln Ser Lys Phe Glu
145                 150                 155                 160

Glu Lys Glu Leu Lys Tyr Glu Gly Gly Ala Glu Lys Ser Lys Ile Glu
                165                 170                 175

Asp Phe Ile Arg Glu Asn Tyr His Gly Leu Val Gly His Arg Thr Ser
                180                 185                 190

Asp Asn Phe Gln Asp Phe Lys Asn Pro Leu Val Val Ala Tyr Tyr Asp
            195                 200                 205

Val Asp Tyr Val Lys Asn Thr Lys Gly Thr Asn Tyr Trp Arg Asn Arg
210                 215                 220

Ile Met Lys Val Ala Gln His Phe Lys Asp Lys Leu Asn Phe Ala Val
225                 230                 235                 240

Ser Asn Ile Asn Gln Phe Ser Ala Glu Ile Glu Glu Phe Gly Leu Thr
            245                 250                 255

Val Lys Gly Asp Lys Pro Ala Ile Ala Val Arg Asn Glu Lys Gln Gln
            260                 265                 270

Lys Phe Arg Met Thr Asp Glu Ser Met Asp Ala Phe Glu Lys Phe
    275                 280                 285

Leu Lys Asp Phe Leu Asp Gly Lys Leu Glu Ala His Val Lys Ser Glu
290                 295                 300

Pro Ile Pro Glu Asn Asn Asp Gly Pro Val Lys Val Ala Val Ala Ser
305                 310                 315                 320

Asn Phe Asp Asp Ile Val Thr Asn Asn Asp Lys Asp Ile Leu Leu Glu
                325                 330                 335

Phe Tyr Ala Pro Trp Cys Gly His Cys Lys Lys Leu Ala Pro Thr Tyr
                340                 345                 350

Glu Glu Leu Gly Thr Glu Met Lys Gln Glu Asp Val Glu Ile Val Lys
            355                 360                 365

Met Asp Ala Thr Ala Asn Asp Val Pro Pro Tyr Glu Val His Gly
370                 375                 380

Phe Pro Thr Leu Tyr Trp Val Pro Lys Asn Ser Lys Asn Asn Pro Lys
385                 390                 395                 400

Lys Tyr Asp Gly Gly Arg Glu Leu Asp Asp Leu Ile Lys Tyr Ile Ser
                405                 410                 415

Lys His Ala Thr Asn Glu Leu Lys Gly Trp Asp Arg Lys Gly Thr Lys
```

Lys Ser Glu Lys Thr Glu Leu
        435

<210> SEQ ID NO 13
<211> LENGTH: 1759
<212> TYPE: DNA
<213> ORGANISM: Scolopendra canidens DS

<400> SEQUENCE: 13

```
gcacgaggtg aattgccatt tcaccgggtg gagatagaac ggaatttata ttttttttaa      60
ttgaaaatgt ggaaaatcgt tgcttttttcc tgcttttttg tagcgactat tgctagtgat    120
gtcttagaat ttaccgattc tgattttgac gaaaggatca agaacatga tacttattta     180
gtcgagtttt atgcaccatg gtgtgggcat tgtaaacgct tagctccaga atatgaaaaa    240
gcagctacaa ttctaaaaga taatgatcca cccattcctc ttgttaaggt tgattgtatc    300
gaatctggaa agaaacttg tgggaaattt ggagtttccg gttacccaac tctaaaaatt    360
tttagaaatg gagacttttc acaagaatac aatggaccaa gagaagcaaa tggaattgta   420
aaatatatgg ctgcccaagt tgggccaagt tcgaaagaat tccagaatgt gaaagaagta   480
cagcaattcc ttgaaaaaga gaagttgca attattggat tttttgaatc tgaagatgct   540
aaactcaaag caacattcca aaagtagca gataaattga gagaaactgc aagatttggt   600
cattcttaca attcattggt gttgaaggaa tatggttata caatcaagt tgtattattt   660
cggcctaaac atcttcaaag taagtttgaa gattctcaag tggtatatga tggagacaaa   720
agtgataaac aggagcttga agaatttgtt aacaaaaatt accatggttt agtgggtcat   780
aggacaacag acaatactaa tcaattctct cctccattga tagtatcata ttataaagtt   840
gattatgtta agaacaccaa aggtaccaat tattggcgta atcgtatcat gaaagttgca   900
tcagaattca aaggcgcctt gaattttgcc atttcaaata aagatgaatt tacacatgaa   960
ttaagcgaat atggttttaa ctatgtggct ggagataaac cagttgttgc tgctcgaaat  1020
gcaaaatctg agaaatttgt aatggaaggc gaatttccaa taccaagctt tgaaaagttc  1080
attaaggact ttttagatga aaaactaaaa ccatacttaa agtctgagcc aattccagag  1140
aaaatgaag agcctgttaa ggttgctgtt gctcaaaaatt ttgaagagtt agtcaccaag  1200
agtgataaag atgtattgat tgaattctat gctccatggt gtggacattg taaaaaatta  1260
gcacctgttt atgatgaatt aggcaaagcc ttggaaggag aaacaacagt agaaatagtt  1320
aaaatggatg ccacagcaaa tgatgtgcct tcaccttatg aagtgcatgg tttccctact  1380
ttatattggg ctccacgtga taagaaagat aagcctgtcc gatacgatgg tggacgagaa  1440
ttggatgatt tcattaaata tattgctaag cattccacag atgaacttaa aacttacaac  1500
agaaatggga aaagaaaaa agttgaattg taaagtagca atttagaatt taaaatattt  1560
gttcagtaaa agcacaattt tttattttta agggaataaa aatgtaaaaa tcaattatga  1620
taatttaaaa tttagagtgc tttatgttgg tggtacgtat tgtctttatt tctttgtaag  1680
ataaaatgtt gaaattaat tcgaaataaa attttttttaa taaattagtt tttacaaaaa  1740
gaaaaaaaaa aaaaaaaa                                                  1759
```

<210> SEQ ID NO 14
<211> LENGTH: 488
<212> TYPE: PRT
<213> ORGANISM: Scolopendra canidens DS

<400> SEQUENCE: 14

```
Met Trp Lys Ile Val Ala Phe Ser Cys Phe Val Ala Thr Ile Ala
 1               5                  10                  15

Ser Asp Val Leu Glu Phe Thr Asp Ser Asp Phe Asp Glu Arg Ile Lys
                20                  25                  30

Glu His Asp Thr Tyr Leu Val Glu Phe Tyr Ala Pro Trp Cys Gly His
             35                  40                  45

Cys Lys Arg Leu Ala Pro Glu Tyr Glu Lys Ala Ala Thr Ile Leu Lys
 50                  55                  60

Asp Asn Asp Pro Pro Ile Pro Leu Val Lys Val Asp Cys Ile Glu Ser
 65                  70                  75                  80

Gly Lys Glu Thr Cys Gly Lys Phe Gly Val Ser Gly Tyr Pro Thr Leu
                 85                  90                  95

Lys Ile Phe Arg Asn Gly Asp Phe Ser Gln Glu Tyr Asn Gly Pro Arg
                100                 105                 110

Glu Ala Asn Gly Ile Val Lys Tyr Met Ala Ala Gln Val Gly Pro Ser
            115                 120                 125

Ser Lys Glu Phe Gln Asn Val Lys Glu Val Gln Gln Phe Leu Glu Lys
    130                 135                 140

Glu Glu Val Ala Ile Ile Gly Phe Phe Glu Ser Glu Asp Ala Lys Leu
145                 150                 155                 160

Lys Ala Thr Phe Gln Lys Val Ala Asp Lys Leu Arg Glu Thr Ala Arg
                165                 170                 175

Phe Gly His Ser Tyr Asn Ser Leu Val Leu Lys Glu Tyr Gly Tyr Thr
                180                 185                 190

Asn Gln Val Val Leu Phe Arg Pro Lys His Leu Gln Ser Lys Phe Glu
            195                 200                 205

Asp Ser Gln Val Val Tyr Asp Gly Asp Lys Ser Asp Lys Gln Glu Leu
    210                 215                 220

Glu Glu Phe Val Asn Lys Asn Tyr His Gly Leu Val Gly His Arg Thr
225                 230                 235                 240

Thr Asp Asn Thr Asn Gln Phe Ser Pro Pro Leu Ile Val Ser Tyr Tyr
                245                 250                 255

Lys Val Asp Tyr Val Lys Asn Thr Lys Gly Thr Asn Tyr Trp Arg Asn
                260                 265                 270

Arg Ile Met Lys Val Ala Ser Glu Phe Lys Gly Arg Leu Asn Phe Ala
            275                 280                 285

Ile Ser Asn Lys Asp Glu Phe Thr His Glu Leu Ser Glu Tyr Gly Phe
    290                 295                 300

Asn Tyr Val Ala Gly Asp Lys Pro Val Val Ala Ala Arg Asn Ala Lys
305                 310                 315                 320

Ser Glu Lys Phe Val Met Glu Gly Glu Phe Ser Ile Pro Ser Phe Glu
                325                 330                 335

Lys Phe Ile Lys Asp Phe Leu Asp Glu Lys Leu Lys Pro Tyr Leu Lys
                340                 345                 350

Ser Glu Pro Ile Pro Glu Lys Asn Glu Glu Pro Val Lys Val Ala Val
    355                 360                 365

Ala Gln Asn Phe Glu Glu Leu Val Thr Lys Ser Asp Lys Asp Val Leu
    370                 375                 380

Ile Glu Phe Tyr Ala Pro Trp Cys Gly His Cys Lys Lys Leu Ala Pro
385                 390                 395                 400

Val Tyr Asp Glu Leu Gly Lys Ala Leu Glu Gly Glu Thr Thr Val Glu
                405                 410                 415
```

Ile Val Lys Met Asp Ala Thr Ala Asn Asp Val Pro Ser Pro Tyr Glu
                420                 425                 430

Val His Gly Phe Pro Thr Leu Tyr Trp Ala Pro Arg Asp Lys Lys Asp
        435                 440                 445

Lys Pro Val Arg Tyr Asp Gly Arg Glu Leu Asp Asp Phe Ile Lys
    450                 455                 460

Tyr Ile Ala Lys His Ser Thr Asp Glu Leu Lys Thr Tyr Asn Arg Asn
465                 470                 475                 480

Gly Lys Lys Lys Lys Val Glu Leu
                485

<210> SEQ ID NO 15
<211> LENGTH: 1498
<212> TYPE: DNA
<213> ORGANISM: Hottentotta judiaca

<400> SEQUENCE: 15

| | | | | | |
|---|---|---|---|---|---|
| agatctgtaa | ggtcatgaat | tttggtaatt | tattaatctt | tttttctttt | ttaatagtcg | 60 |
| tattaggtga | agttagagaa | gacaatgtat | tagttttgaa | taaagaaaat | tttgatcatt | 120 |
| caattaaaaa | caacaagtat | atcttagtag | aattttatgc | tccatggtgt | ggacattgta | 180 |
| aagcactagc | tccagaatat | gctaaagctg | caaagctgtt | gttagaagaa | aaatctgaaa | 240 |
| ttcagttagc | aaaaattgat | gcaactgaag | aaacagaatt | agcagagaag | cataaagtaa | 300 |
| aaggttatcc | aacaattaaa | ttcttccgtg | aaggtgatcc | tattgattat | acaggtggcc | 360 |
| gtactggtga | tgatattgta | acttggttga | agaaaaaaac | tggacctcca | gctacattat | 420 |
| taagtacagt | tgatgaagca | acaaacttta | agagagtaa | agatgtcgta | attataggat | 480 |
| ttttcaagga | tcaggaaagt | aatcaagcta | agaatatttt | aaatgcagca | tatatgactg | 540 |
| atgatcatcc | atttggtatt | acttcagatg | aaaatgttta | taacatttt | aatgttgaaa | 600 |
| aggatactat | tttcttattt | aagaagtttg | atgagggaa | gaatgaattc | gagggagaat | 660 |
| ttacaaaaga | taacattata | aaattcatta | aactcaacaa | tttaccatta | gtaattgaat | 720 |
| ttagtcaaga | gaatgcacag | aagatatttg | ggggtgacat | aaaaatgcat | aatcttcttt | 780 |
| ttattagtaa | aaagagtaaa | gattttgatg | aaatagtgaa | aacgtttcgt | attgtggcaa | 840 |
| aagaatataa | aaatcagata | ttatttgttg | ttattaatac | tgatgatgaa | gacaatgaaa | 900 |
| aaataactga | attctttggt | ttaaaaaag | atgagcagcc | atcaataaga | ttaattaaac | 960 |
| tagaagaagg | aatgtctaaa | tataaacctg | aaactattga | aatttctgaa | gaaatgttc | 1020 |
| gaaaatttgt | taaggtgtc | ttagatggaa | cagttaaaca | acatctactt | tctcaagaac | 1080 |
| ttcctgaaga | ttgggataag | catccagtta | agtattagt | aaataagaat | ttcgatgaag | 1140 |
| ttgcatttga | taaactaaa | gatgttattg | tagaattcta | tgcaccatgg | tgtggtcatt | 1200 |
| gcaaacagtt | agctccaatt | tatgaagaac | tcggagaaaa | atataaaat | cgaaatgata | 1260 |
| ttattattgc | aaaaatggat | gcaacagcca | atgaattaga | acatacaaaa | attaacagct | 1320 |
| ttcctacaat | taaattatat | aaaaaaggaa | ccaatgaagt | gatagactat | gatggaaaac | 1380 |
| attcacttga | aggacttgtg | aattttattg | attctggtgg | aaaaataaca | aaggaacctg | 1440 |
| aagatgagga | taaatcaaaa | gaaccagatg | ccaaaggaga | tgaattatga | gcggccgc | 1498 |

<210> SEQ ID NO 16
<211> LENGTH: 491
<212> TYPE: PRT
<213> ORGANISM: Hottentotta judiaca -continued

<400> SEQUENCE: 16

```
Met Asn Phe Gly Asn Leu Leu Ile Phe Phe Ser Phe Leu Ile Val Val
  1               5                  10                  15

Leu Gly Glu Val Arg Glu Asp Asn Val Leu Val Leu Asn Lys Glu Asn
             20                  25                  30

Phe Asp His Ser Ile Lys Asn Asn Lys Tyr Ile Leu Val Glu Phe Tyr
         35                  40                  45

Ala Pro Trp Cys Gly His Cys Lys Ala Leu Ala Pro Glu Tyr Ala Lys
 50                  55                  60

Ala Ala Lys Leu Leu Leu Glu Glu Lys Ser Glu Ile Gln Leu Ala Lys
 65                  70                  75                  80

Ile Asp Ala Thr Glu Glu Thr Glu Leu Ala Glu Lys His Lys Val Lys
                 85                  90                  95

Gly Tyr Pro Thr Ile Lys Phe Phe Arg Glu Gly Asp Pro Ile Asp Tyr
            100                 105                 110

Thr Gly Gly Arg Thr Gly Asp Asp Ile Val Thr Trp Leu Lys Lys Lys
            115                 120                 125

Thr Gly Pro Pro Ala Thr Leu Leu Ser Thr Val Asp Glu Ala Thr Asn
130                 135                 140

Phe Lys Glu Ser Lys Asp Val Val Ile Ile Gly Phe Phe Lys Asp Gln
145                 150                 155                 160

Glu Ser Asn Gln Ala Lys Glu Tyr Leu Asn Ala Ala Tyr Met Thr Asp
                165                 170                 175

Asp His Pro Phe Gly Ile Thr Ser Asp Glu Asn Val Tyr Lys His Phe
            180                 185                 190

Asn Val Glu Lys Asp Thr Ile Phe Leu Phe Lys Lys Phe Asp Glu Gly
            195                 200                 205

Lys Asn Glu Phe Glu Gly Glu Phe Thr Lys Asp Asn Ile Ile Lys Phe
210                 215                 220

Ile Lys Leu Asn Asn Leu Pro Leu Val Ile Glu Phe Ser Gln Glu Asn
225                 230                 235                 240

Ala Gln Lys Ile Phe Gly Gly Asp Ile Lys Met His Asn Leu Leu Phe
                245                 250                 255

Ile Ser Lys Lys Ser Lys Asp Phe Asp Glu Ile Val Lys Thr Phe Arg
            260                 265                 270

Ile Val Ala Lys Glu Tyr Lys Asn Gln Ile Leu Phe Val Val Ile Asn
            275                 280                 285

Thr Asp Asp Glu Asp Asn Glu Lys Ile Thr Glu Phe Phe Gly Leu Lys
290                 295                 300

Lys Asp Glu Gln Pro Ser Ile Arg Leu Ile Lys Leu Glu Glu Gly Met
305                 310                 315                 320

Ser Lys Tyr Lys Pro Glu Thr Ile Glu Ile Ser Glu Glu Asn Val Arg
                325                 330                 335

Lys Phe Val Lys Gly Val Leu Asp Gly Thr Val Lys Gln His Leu Leu
            340                 345                 350

Ser Gln Glu Leu Pro Glu Asp Trp Asp Lys His Pro Val Lys Val Leu
        355                 360                 365

Val Asn Lys Asn Phe Asp Glu Val Ala Phe Asp Lys Thr Lys Asp Val
    370                 375                 380

Ile Val Glu Phe Tyr Ala Pro Trp Cys Gly His Cys Lys Gln Leu Ala
385                 390                 395                 400

Pro Ile Tyr Glu Glu Leu Gly Glu Lys Tyr Lys Asn Arg Asn Asp Ile
```

| | 405 | | | | 410 | | | | 415 | | |
|---|---|---|---|---|---|---|---|---|---|---|---|
| Ile | Ile | Ala | Lys | Met | Asp | Ala | Thr | Ala | Asn | Glu | Leu | Glu | His | Thr | Lys |
| | | | 420 | | | | 425 | | | | 430 | |

Ile Asn Ser Phe Pro Thr Ile Lys Leu Tyr Lys Lys Gly Thr Asn Glu
            435                 440                 445

Val Ile Asp Tyr Asp Gly Lys His Ser Leu Glu Gly Leu Val Asn Phe
    450                 455                 460

Ile Asp Ser Gly Gly Lys Ile Thr Lys Glu Pro Glu Asp Glu Asp Lys
465                 470                 475                 480

Ser Lys Glu Pro Asp Ala Lys Gly Asp Glu Leu
                485                 490

```
<210> SEQ ID NO 17
<211> LENGTH: 1498
<212> TYPE: DNA
<213> ORGANISM: Hottentotta judiaca

<400> SEQUENCE: 17
agatctgtaa ggtcatgaat tttggtaatt tattaatctt ttttctttt ttaatagtcg      60 tattaggtga agttagagag gacaatgtat tagttttgaa taaagaaaat tttgatcatt    120
caattaaaaa caacaagtat atcttagtag aatttttatgc tccatggtgt ggacattgta   180
aagcactagc tccagaatat gctaaagctg caaagctgtt gttagaagaa aaatctgaaa    240
ttcagttagc aaaaattgat gcaactgaag aaacagaatt agcagagaag cataaagtaa    300
aaggttatcc aacaattaaa ttcttccgtg aaggtgatcc tattgattat acaggtggcc    360
gtactggtga tgatattgta acttggttga agaaaaaaac tggacctcca gctacattat    420
taagtacagt tgatgaagca acaaacttta agagagtaa agatgtcgta attataggat    480
ttttcaagga tcaggaaagt aatcaagcta agaatatttt aaatgcagca tatatgactg    540
atgatcatcc atttggtatt acttcagatg aaaatgttta taacatttt aatgttgaaa     600 aggatactat tttcttattt aagaagtttg atgaggggaa gaatgaattc gagggagaat    660
ttacaaaaga taacattata aaattcatta aactcaacaa tttaccatta gtaattgaat    720
ttagtcaaga gaatgcacag aagatatttg ggggtgacat aaaaatgcat aatcttcttt    780
ttattagtaa aaagagtaaa gattttgatg aaatagtgaa aacgtttcgt attgtggcaa    840 agaatataa aaatcagata ttattgtttg ttattaatac tgatgatgaa ggcaatggac     900
aaataactga attctttggt ttaaaaaagg atgagcagcc atcaataaga ttaattaaac    960
tagaagaagg aatgtctaaa tataaacctg aaactattga aatttctgaa gaaaatgttc   1020
gaaaatttgt taaaggtgtc ttagatggaa cagttaaaca acatctactt tctcaagaac   1080
ttcctgaaga ttgggataag catccagtta aagtattagt aaataagaat ttcgatgaag   1140
ttgcatttga taaaactaaa gatgttattg tagaattcta tgcaccatgg tgtggtcatt   1200
gcaaacagtt agctccaatt tatgaagaac tcggagaaaa atataaaaat cgaaatgata   1260
ttattattgc aaaaatggat gcaacagcca atgaattaga acatacaaaa attaacagct   1320
ttcctacaat taaattatat aaaaaaggaa ccaatgaagt gatagactat gatggaaaac   1380
attcacttga aggacttgtg aatttttattg attctggtgg aaaaataaca aaggaacctg   1440
aagatgagga taaatcaaaa gaaccagatg ccaaaagaga tgaattatga gcggccgc    1498

<210> SEQ ID NO 18
<211> LENGTH: 491
<212> TYPE: PRT
```

<213> ORGANISM: Hottentotta judiaca

<400> SEQUENCE: 18

```
Met Asn Phe Gly Asn Leu Leu Ile Phe Ser Phe Leu Ile Val Val
 1               5                  10                  15

Leu Gly Glu Val Arg Glu Asp Asn Val Leu Val Leu Asn Lys Glu Asn
                20                  25                  30

Phe Asp His Ser Ile Lys Asn Asn Lys Tyr Ile Leu Val Glu Phe Tyr
            35                  40                  45

Ala Pro Trp Cys Gly His Cys Lys Ala Leu Ala Pro Glu Tyr Ala Lys
        50                  55                  60

Ala Ala Lys Leu Leu Leu Glu Glu Lys Ser Glu Ile Gln Leu Ala Lys
65                  70                  75                  80

Ile Asp Ala Thr Glu Glu Thr Glu Leu Ala Glu Lys His Lys Val Lys
                85                  90                  95

Gly Tyr Pro Thr Ile Lys Phe Phe Arg Glu Gly Asp Pro Ile Asp Tyr
            100                 105                 110

Thr Gly Gly Arg Thr Gly Asp Asp Ile Val Thr Trp Leu Lys Lys Lys
        115                 120                 125

Thr Gly Pro Pro Ala Thr Leu Leu Ser Thr Val Asp Glu Ala Thr Asn
130                 135                 140

Phe Lys Glu Ser Lys Asp Val Val Ile Ile Gly Phe Phe Lys Asp Gln
145                 150                 155                 160

Glu Ser Asn Gln Ala Lys Glu Tyr Leu Asn Ala Ala Tyr Met Thr Asp
                165                 170                 175

Asp His Pro Phe Gly Ile Thr Ser Asp Glu Asn Val Tyr Lys His Phe
            180                 185                 190

Asn Val Glu Lys Asp Thr Ile Phe Leu Phe Lys Lys Phe Asp Glu Gly
        195                 200                 205

Lys Asn Glu Phe Glu Gly Glu Phe Thr Lys Asp Asn Ile Ile Lys Phe
        210                 215                 220

Ile Lys Leu Asn Asn Leu Pro Leu Val Ile Glu Phe Ser Gln Glu Asn
225                 230                 235                 240

Ala Gln Lys Ile Phe Gly Gly Asp Ile Lys Met His Asn Leu Leu Phe
                245                 250                 255

Ile Ser Lys Lys Ser Lys Asp Phe Asp Glu Ile Val Lys Thr Phe Arg
            260                 265                 270

Ile Val Ala Lys Glu Tyr Lys Asn Gln Ile Leu Phe Val Val Ile Asn
        275                 280                 285

Thr Asp Asp Glu Gly Asn Gly Gln Ile Thr Glu Phe Phe Gly Leu Lys
290                 295                 300

Lys Asp Glu Gln Pro Ser Ile Arg Leu Ile Lys Leu Glu Glu Gly Met
305                 310                 315                 320

Ser Lys Tyr Lys Pro Glu Thr Ile Glu Ile Ser Glu Glu Asn Val Arg
                325                 330                 335

Lys Phe Val Lys Gly Val Leu Asp Gly Thr Val Lys Gln His Leu Leu
            340                 345                 350

Ser Gln Glu Leu Pro Glu Asp Trp Asp Lys His Pro Val Lys Val Leu
        355                 360                 365

Val Asn Lys Asn Phe Asp Glu Val Ala Phe Asp Lys Thr Lys Asp Val
        370                 375                 380

Ile Val Glu Phe Tyr Ala Pro Trp Cys Gly His Cys Lys Gln Leu Ala
385                 390                 395                 400
```

```
Pro Ile Tyr Glu Glu Leu Gly Glu Lys Tyr Lys Asn Arg Asn Asp Ile
                405                 410                 415
Ile Ile Ala Lys Met Asp Ala Thr Ala Asn Glu Leu Glu His Thr Lys
            420                 425                 430
Ile Asn Ser Phe Pro Thr Ile Lys Leu Tyr Lys Lys Gly Thr Asn Glu
        435                 440                 445
Val Ile Asp Tyr Asp Gly Lys His Ser Leu Glu Gly Leu Val Asn Phe
    450                 455                 460
Ile Asp Ser Gly Gly Lys Ile Thr Lys Glu Pro Glu Asp Glu Asp Lys
465                 470                 475                 480
Ser Lys Glu Pro Asp Ala Lys Arg Asp Glu Leu
                485                 490

<210> SEQ ID NO 19
<211> LENGTH: 802
<212> TYPE: DNA
<213> ORGANISM: Hottentotta judiaca

<400> SEQUENCE: 19
gcacgaggga acatgggatg ttacttgttg gtgttgttga tatttttatt ctttctacga      60
gatagtcaaa gtagcagtga tttatacacg gataactcga taaaatatga cgaggaagga    120
tttaggagga atataggaaa tatagtgcat tttgttaaat tttacgcccc ttggtgtgga    180
cattgtaaaa gattagcacc aatttgggat gaattagcag agaaatataa taaacctgga    240
gaacagaagc ttgttattgc taaaattgat tgtacaactg aaactgctct tgttctgaa     300
caaggaatta ctggttatcc cacattaaag ttttttaaga aggtacaac tgaaggacat     360
aaatatagag gtccacgtga cattacttct ttagaagctt ttattgccaa tagcttagga    420
cacgaagagg ctattaaaaa atctcctgaa cctccaaaat tcataaatga aattattcag    480
ttaagtgaca atacttttca taaatttgta gcaaaaggac ttcattttgt taaatttttat   540
gctccttggt gtggtcactg tcagaaactt gttcccattt ggaaagaatt ggcaaatagc    600
tttaaatttg atacatccat aaaaatatct gagattgatt gcactacaca acatttagta    660
tgtaatgaat ttgaagttaa agcatatcca actttattgt ggattgttga tggtaaaaag    720
attgaaaagt atgaaggaat gagatcccat gaagaactaa aattatttat taataaaatg    780
aaagaaaaaa aaaaaaaaaa aa                                              802

<210> SEQ ID NO 20
<211> LENGTH: 244
<212> TYPE: PRT
<213> ORGANISM: Hottentotta judiaca

<400> SEQUENCE: 20

Met Gly Cys Tyr Leu Leu Val Leu Leu Ile Phe Leu Phe Phe Leu Arg
1               5                   10                  15
Asp Ser Gln Ser Ser Asp Leu Tyr Thr Asp Asn Ser Ile Lys Tyr
            20                  25                  30
Asp Glu Glu Gly Phe Arg Arg Asn Ile Gly Asn Ile Val His Phe Val
        35                  40                  45
Lys Phe Tyr Ala Pro Trp Cys Gly His Cys Lys Arg Leu Ala Pro Ile
    50                  55                  60
Trp Asp Glu Leu Ala Glu Lys Tyr Asn Lys Pro Gly Glu Gln Lys Leu
65                  70                  75                  80
Val Ile Ala Lys Ile Asp Cys Thr Thr Glu Thr Ala Leu Cys Ser Glu
                85                  90                  95
```

```
Gln Gly Ile Thr Gly Tyr Pro Thr Leu Lys Phe Phe Lys Lys Gly Thr
            100                 105                 110

Thr Glu Gly His Lys Tyr Arg Gly Pro Arg Asp Ile Thr Ser Leu Glu
        115                 120                 125

Ala Phe Ile Ala Asn Ser Leu Gly His Glu Glu Ala Ile Lys Lys Ser
    130                 135                 140

Pro Glu Pro Pro Lys Phe Ile Asn Glu Ile Ile Gln Leu Ser Asp Asn
145                 150                 155                 160

Thr Phe His Lys Phe Val Ala Lys Gly Leu His Phe Val Lys Phe Tyr
                165                 170                 175

Ala Pro Trp Cys Gly His Cys Gln Lys Leu Val Pro Ile Trp Lys Glu
            180                 185                 190

Leu Ala Asn Ser Phe Lys Phe Asp Thr Ser Ile Lys Ile Ser Glu Ile
                195                 200                 205

Asp Cys Thr Thr Gln His Leu Val Cys Asn Glu Phe Glu Val Lys Ala
            210                 215                 220

Tyr Pro Thr Leu Leu Trp Ile Val Asp Gly Lys Lys Ile Glu Lys Tyr
225                 230                 235                 240

Glu Gly Met Arg

<210> SEQ ID NO 21
<211> LENGTH: 1495
<212> TYPE: DNA
<213> ORGANISM: Heliothus virescens]

<400> SEQUENCE: 21
gcacgagaaa cccgatcgtt catcagaaaa gtcggactct gacgtgatca cgctgacgga    60
tgagaacttc aagaagctgg tgctggacag cgaagacctg tggctggttg agttctacgc   120
gccctggtgc ggtcactgca agaatttgaa gccccagtgg gccaaggctg ccaaagaact   180
taagggcaag gtgaaactcg agcattagac gcgacagtc accaagcga tggcttcccg     240 ctaccaagtg caaggctacc ccaccatcaa gctgttccca tctggcaaga agtccagtga   300
ctccgcagag gactacaatg gaggcaggac cgccagcgac atcgtgactt atgctcttga   360
caagctcgct gaaacgtgc ccgctcctga gatcgttcag gttatcgacg aagcgtcaat    420
gcaggcgtgc agtgaaaaac cgctgtgcgt ggtatcggtt ctgccgcaca tcttggactg   480
caacgcggcc tgtcgcaacg aataccagc gatactcgca cgactcggtg acaagtacaa    540
gagcaagatg tggggatggg tgtgggccga agctggcgcg cagatatctt ggaagagtc    600 gctggagctg gcggtttcg gttaccccgc catggctgtc gtcaacgcta agaaactcaa    660
gttctcaacc ctcaggggat ccttctccga gactggcatc aatgaattcc ttagggatct   720
atcattcggt cgcggacaga ctgccccagt gaagggcgca gagatgccga gatcgtgtc    780 caccgacccc tgggacggca aggacggtga actgccacaa gaagaggaca ttgacctctc   840
tgacgtagac ctcgagaagg acgagttata agtgcagcag ccatgttgct aacagtctgg   900
actttataaa acccaacggt tgagtgttct gtaacaagta cgcttctaca caaaatcata   960
tcagtaaaaa tctctgattt taaacttaag aaagtgatac aagttcaagc atttaacagt  1020
ttaggttact atttattttc accagtgagc tagtaacttt gtacctaata atatggttca  1080
gtttaaaatt atgctgtttt aaatatcgaa ggagaagctt aattccatca catactatga  1140 atttttatttt ctgaaacatt tttaggtgtt tgataatcac aatttagtac cagccatata  1200
tttcgtgtgt agctcggcgc gagcgagtgg tgcaacgact gatcttttg aatcattgtt   1260
```

-continued

```
atttgtatgt atatccttca tagtcataaa attgataaca caaactgata cttaatttta   1320
gttggattag acattaattg gagtgtacat tagctaaacg ccaatcttcc aatattatgt   1380
ttaattttgg taagcattta ttgttgtgag gagatttgga taattttatg aattgataaa   1440
tcgctaataa atttttaata aaaaaaaaaa aaaaagagag agagagagaa ctagt        1495

<210> SEQ ID NO 22
<211> LENGTH: 289
<212> TYPE: PRT
<213> ORGANISM: Heliothus virescens]

<400> SEQUENCE: 22

His Glu Lys Pro Asp Arg Ser Ser Glu Lys Ser Asp Ser Asp Val Ile
  1               5                  10                  15

Thr Leu Thr Asp Glu Asn Phe Lys Lys Leu Val Leu Asp Ser Glu Asp
             20                  25                  30

Leu Trp Leu Val Glu Phe Tyr Ala Pro Trp Cys Gly His Cys Lys Asn
         35                  40                  45

Leu Lys Pro Gln Trp Ala Lys Ala Ala Lys Glu Leu Lys Gly Lys Val
     50                  55                  60

Lys Leu Gly Ala Leu Asp Ala Thr Val His Gln Ala Met Ala Ser Arg
 65                  70                  75                  80

Tyr Gln Val Gln Gly Tyr Pro Thr Ile Lys Leu Phe Pro Ser Gly Lys
                 85                  90                  95

Lys Ser Ser Asp Ser Ala Glu Asp Tyr Asn Gly Gly Arg Thr Ala Ser
            100                 105                 110

Asp Ile Val Thr Tyr Ala Leu Asp Lys Leu Ala Glu Asn Val Pro Ala
        115                 120                 125

Pro Glu Ile Val Gln Val Ile Asp Glu Ala Ser Met Gln Ala Cys Ser
    130                 135                 140

Glu Lys Pro Leu Cys Val Val Ser Val Leu Pro His Ile Leu Asp Cys
145                 150                 155                 160

Asn Ala Ala Cys Arg Asn Glu Tyr Leu Ala Ile Leu Ala Arg Leu Gly
                165                 170                 175

Asp Lys Tyr Lys Ser Lys Met Trp Gly Trp Val Trp Ala Glu Ala Gly
            180                 185                 190

Ala Gln Ile Ser Leu Glu Glu Ser Leu Glu Leu Gly Gly Phe Gly Tyr
        195                 200                 205

Pro Ala Met Ala Val Val Asn Ala Lys Lys Leu Lys Phe Ser Thr Leu
    210                 215                 220

Arg Gly Ser Phe Ser Glu Thr Gly Ile Asn Glu Phe Leu Arg Asp Leu
225                 230                 235                 240

Ser Phe Gly Arg Gly Gln Thr Ala Pro Val Lys Gly Ala Glu Met Pro
                245                 250                 255

Lys Ile Val Ser Thr Asp Pro Trp Asp Gly Lys Asp Gly Glu Leu Pro
            260                 265                 270

Gln Glu Glu Asp Ile Asp Leu Ser Asp Val Asp Leu Glu Lys Asp Glu
        275                 280                 285

Leu

<210> SEQ ID NO 23
<211> LENGTH: 473
<212> TYPE: DNA
<213> ORGANISM: Vaejovis carolinianus
<220> FEATURE:
```

```
<221> NAME/KEY: unsure
<222> LOCATION: (408)
<221> NAME/KEY: unsure
<222> LOCATION: (442)
<221> NAME/KEY: unsure
<222> LOCATION: (444)

<400> SEQUENCE: 23
gttgtcatct gttttagtt ttaatgttgc aatatatgct agtagtgact tatacgttga       60
caattcgtta aaatatgatg aagatggttt tagggaaaat gtaggaaaat tgacgctttt      120
tgtgaaattc tacgcccctt ggtgtggaca ttgtaaaaga ttggctccta cttgggacga     180
actagctgaa aaatataata ttcaaccaga aaacaacag gtcataatag ctaagattga      240
ctgtacatca gagacagctc tttgttctga gcaaggaata acaggttatc caacattaaa    300
gttttttaag aaaggtgaaa ctgaaggaac aaaatacagg ggaccaagag acatcacatc     360
tttagaagct tttattgcta acagcttggg caaagaagag gctgtggnaa gatcttaaac    420
caccaagaac caagtaaatg gncnaataag aattaactga tgaaacattc cac          473

<210> SEQ ID NO 24
<211> LENGTH: 343
<212> TYPE: PRT
<213> ORGANISM: Vaejovis carolinianus

<400> SEQUENCE: 24

Thr Arg Leu Ser Ser Val Phe Ser Phe Asn Val Ala Ile Tyr Ala Ser
  1               5                  10                  15

Ser Asp Leu Tyr Val Asp Asn Ser Leu Lys Tyr Asp Glu Asp Gly Phe
                 20                  25                  30

Arg Glu Asn Val Gly Lys Leu Thr Leu Phe Val Lys Phe Tyr Ala Pro
             35                  40                  45

Trp Cys Gly His Cys Lys Arg Leu Ala Pro Thr Trp Asp Glu Leu Ala
         50                  55                  60

Glu Lys Tyr Asn Ile Gln Pro Glu Lys Gln Gln Val Ile Ile Ala Lys
 65                  70                  75                  80

Ile Asp Cys Thr Ser Glu Thr Ala Leu Cys Ser Glu Gln Gly Ile Thr
                 85                  90                  95

Gly Tyr Pro Thr Leu Lys Phe Phe Lys Lys Gly Glu Thr Glu Gly Thr
            100                 105                 110

Lys Tyr Arg Gly Pro Arg Asp Ile Thr Ser Leu Glu Ala Phe Ile Ala
        115                 120                 125

Asn Ser Leu Gly Lys Glu Glu Ala Val Glu Asp Leu Lys Pro Pro Glu
130                 135                 140

Pro Val Asn Gly Leu Ile Glu Leu Thr Asp Glu Thr Phe His Lys Thr
145                 150                 155                 160

Ile Glu Arg Gly Tyr His Phe Val Lys Phe Tyr Ala Pro Trp Cys Gly
                165                 170                 175

His Cys Gln Lys Leu Ala Pro Val Trp Gln Gln Leu Ala Asn Ser Phe
            180                 185                 190

Gln His Asp Leu Ser Val Lys Ile Leu Lys Ile Asp Cys Thr Ala His
        195                 200                 205

Arg Leu Ser Cys Asn Glu Phe Glu Val Lys Ala Tyr Pro Thr Leu Leu
    210                 215                 220

Trp Ile Val Asp Gly Lys Lys Val Glu Ile Tyr Gln Gly Ser Arg Thr
225                 230                 235                 240

His Glu Asp Leu Lys Leu Phe Val Asp Lys Met Arg Arg Gln Glu His
```

|  | 245 |  |  |  | 250 |  |  |  |  | 255 |  |  |
|---|---|---|---|---|---|---|---|---|---|---|---|---|
| Glu | Thr | Asp | Ser | Gly | Gly | Glu | His | Gly | Lys | Ile | Pro | Glu | Ser | Leu | Pro |
|  |  |  | 260 |  |  |  | 265 |  |  |  |  | 270 |  |  |  |

| Lys | Pro | Glu | Ala | Pro | Val | Ala | Gln | Leu | Val | Ala | Ser | Asn | Phe | Glu | Asp |
|---|---|---|---|---|---|---|---|---|---|---|---|---|---|---|---|
|  |  | 275 |  |  |  |  | 280 |  |  |  |  | 285 |  |  |  |

| Ser | Ile | Lys | Asn | Gly | Val | Thr | Phe | Val | Lys | Phe | Phe | Ala | Pro | Trp | Cys |
|---|---|---|---|---|---|---|---|---|---|---|---|---|---|---|---|
|  | 290 |  |  |  |  | 295 |  |  |  |  | 300 |  |  |  |  |

| Gly | His | Cys | Arg | Lys | Leu | Ala | Pro | Ile | Trp | Asp | Glu | Leu | Ser | Trp | Glu |
|---|---|---|---|---|---|---|---|---|---|---|---|---|---|---|---|
| 305 |  |  |  | 310 |  |  |  |  | 315 |  |  |  |  |  | 320 |

| Phe | Ile | Asp | Asn | Glu | Asn | Gly | Lys | Ile | Ala | Gln | Val | Asp | Cys | Ser | Ser |
|---|---|---|---|---|---|---|---|---|---|---|---|---|---|---|---|
|  |  |  |  | 325 |  |  |  |  | 330 |  |  |  |  | 335 |  |

| Gln | Glu | Ser | Leu | Cys | Ser | Lys |
|---|---|---|---|---|---|---|
|  |  |  | 340 |  |  |  |

<210> SEQ ID NO 25
<211> LENGTH: 2209
<212> TYPE: DNA
<213> ORGANISM: Spodoptera frugiperda

<400> SEQUENCE: 25

```
gcacgagata agttgtgcga tctcattaaa aaatagtcgg tgttttttata gttttttaaat    60
taagtagaat ataatcaaca caatgttaca cacctatttc ctgggtattt tattgtgtgt   120
ggggtctggg ttggcgttgt atgactccag ttcggacgtg gtggacctga cacccgacaa   180
tttctatcaa ctagtcacag atagagatga tgtatggttg gtggaattct acgcgccgtg   240
gtgcggtcac tgcaagaact tggtgcctga atacaagaaa gcggccaaag ctctgaaggg   300
tattgttaaa gtgggagcta tagacgcaga caagcacaga agcttcgcaa aggactatgg   360
agtgtctggc ttccccacaa ttaagatctt tacgggtcgt aaacatgttc catacaaggg   420
cgcaaggtca gctgatgctt tcgttgatgc tgctctaagt gcagtgaaga gcaaggctta   480
tgagagactt ggaaagagat ccgatgactc atcacacaag tcatccgact ctgacgtgat   540
cacgctgaca gacgacaact tcaagaaact ggtgttggac agcgatgacc tgtggttggt   600
ggagttcttc gccccatggt gcggacactg caagaacctc gagccacact gggctaaggc   660
agctactgaa cttaagggca aggtgaaagt gggagctctc gacgctactg ttcaccagga   720
gatggcaggc cgcttccaag tccaaggcta cccaaccatc aagtacttcc catcaggcaa   780
gaagacctac gactctgctg aggactacaa cggaggcagg acatccagtg acatcgtgtc   840
attcgccctc gaaaagctgg ctgagaatgt acccgctcct gagattattc aggttgtcaa   900
cgaagcaaca atgcaggcgt gcagcgagaa gccgctgtgt gtggtatcgg tgctgcctca   960
catcttcgac tgtaacgcgg cctgccgcaa cgactacctc gccatactcg cccgtctcgg  1020
agacaagtac aagaacaaga tgtggggatg gtatgggct gaagctggtg cccaacttgg  1080
tctagaagag tctctggaac tcggcggctt cggctacccc gccatggctg tggtcaacgc  1140
taagaaactc aagttctcaa cacttagggg atccttctcc gaaactggta tcaacgagtt  1200
ccttagggac ctgtcattcg gtcgcggcca gactgcgcca gtcagaggcg ctgagatgcc  1260
caagatagtg tcgacagacg cttgggacgg caaggacggt gaactgcccc aggaagagga  1320
catagaccta tcagacgtgg accttgagaa ggacgagtta agtgcaaa cagtgactta  1380
gacaagtgta gctaggcggg aatgtccttt gtactgagat caacactcaa tacatactaa  1440
aaaaaacatc ataaaagtta tttaatcact tctagaaggt tccaaagcct agctacgcta  1500
caagatactc gtatctcata aactgtacca gtggttgagt gcatttgaag ttatctgcag  1560
```

-continued

```
tgagaacaca caaataaatt catatcaaat ctctgcttta tagaaagatt gcaggttcga    1620
gcatttgttc atagtatttt attgaagtga gccagtgaat agttttactg ttagataaat    1680
taatatgtaa catagtttga tactatgctg caatacagga actatttatt ccaagctgga    1740
ttaagcatga gttagggtct gtagcaaaat ctacaggcca aaataattaa ggcaatggtg    1800
attttagtta tgcaatttct actctagcta catggttaat ccagccctga ttccatcaca    1860
tgttatttac tttattttct gatatattta gcgtatctga agatcacaaa ttgaaaacgt    1920
aatgtttgga gctgataagc tcggctctag cgagcaatgt aatgactgat gtttctgaat    1980
cattttactt attatttctt attcatgata caaaatataa aaggactgat acctttttta    2040
gttaatgatt ggaattaatt ctccatcagc cattcttcca ataatattgg tttagcgtgg    2100
taagctttta ttgtaatcgt tgtgaggaga tattttggat aattttatga attgtaaaat    2160
cgctaataaa ttttttaatat aattaagtca aaaaaaaaaa aaaaaaaa              2209
```

<210> SEQ ID NO 26
<211> LENGTH: 426
<212> TYPE: PRT
<213> ORGANISM: Spodoptera frugiperda

<400> SEQUENCE: 26

```
Met Leu His Thr Tyr Phe Leu Gly Ile Leu Leu Cys Val Gly Ser Gly
  1               5                  10                  15

Leu Ala Leu Tyr Asp Ser Ser Asp Val Val Asp Leu Thr Pro Asp
             20                  25                  30

Asn Phe Tyr Gln Leu Val Thr Asp Arg Asp Asp Val Trp Leu Val Glu
         35                  40                  45

Phe Tyr Ala Pro Trp Cys Gly His Cys Lys Asn Leu Val Pro Glu Tyr
     50                  55                  60

Lys Lys Ala Ala Lys Ala Leu Lys Gly Ile Val Lys Val Gly Ala Ile
 65                  70                  75                  80

Asp Ala Asp Lys His Arg Ser Phe Ala Lys Asp Tyr Gly Val Ser Gly
                 85                  90                  95

Phe Pro Thr Ile Lys Ile Phe Thr Gly Arg Lys His Val Pro Tyr Lys
            100                 105                 110

Gly Ala Arg Ser Ala Asp Ala Phe Val Asp Ala Ala Leu Ser Ala Val
        115                 120                 125

Lys Ser Lys Ala Tyr Glu Arg Leu Gly Lys Arg Ser Asp Asp Ser Ser
    130                 135                 140

His Lys Ser Ser Asp Ser Asp Val Ile Thr Leu Thr Asp Asp Asn Phe
145                 150                 155                 160

Lys Lys Leu Val Leu Asp Ser Asp Leu Trp Leu Val Glu Phe Phe
                165                 170                 175

Ala Pro Trp Cys Gly His Cys Lys Asn Leu Glu Pro His Trp Ala Lys
            180                 185                 190

Ala Ala Thr Glu Leu Lys Gly Lys Val Lys Val Gly Ala Leu Asp Ala
        195                 200                 205

Thr Val His Gln Glu Met Ala Gly Arg Phe Gln Val Gln Gly Tyr Pro
    210                 215                 220

Thr Ile Lys Tyr Phe Pro Ser Gly Lys Lys Thr Tyr Asp Ser Ala Glu
225                 230                 235                 240

Asp Tyr Asn Gly Gly Arg Thr Ser Ser Asp Ile Val Ser Phe Ala Leu
                245                 250                 255
```

```
Glu Lys Leu Ala Glu Asn Val Pro Ala Pro Glu Ile Ile Gln Val Val
            260                 265                 270

Asn Glu Ala Thr Met Gln Ala Cys Ser Glu Lys Pro Leu Cys Val Val
            275                 280                 285

Ser Val Leu Pro His Ile Phe Asp Cys Asn Ala Ala Cys Arg Asn Asp
            290                 295                 300

Tyr Leu Ala Ile Leu Ala Arg Leu Gly Asp Lys Tyr Lys Asn Lys Met
305                 310                 315                 320

Trp Gly Trp Val Trp Ala Glu Ala Gly Ala Gln Leu Gly Leu Glu Glu
                325                 330                 335

Ser Leu Glu Leu Gly Gly Phe Gly Tyr Pro Ala Met Ala Val Val Asn
            340                 345                 350

Ala Lys Lys Leu Lys Phe Ser Thr Leu Arg Gly Ser Phe Ser Glu Thr
            355                 360                 365

Gly Ile Asn Glu Phe Leu Arg Asp Leu Ser Phe Gly Arg Gly Gln Thr
            370                 375                 380

Ala Pro Val Arg Gly Ala Glu Met Pro Lys Ile Val Ser Thr Asp Ala
385                 390                 395                 400

Trp Asp Gly Lys Asp Gly Glu Leu Pro Gln Glu Glu Asp Ile Asp Leu
                405                 410                 415

Ser Asp Val Asp Leu Glu Lys Asp Glu Leu
            420                 425

<210> SEQ ID NO 27
<211> LENGTH: 496
<212> TYPE: PRT
<213> ORGANISM: Drosophila melanogaster

<400> SEQUENCE: 27

Met Lys Phe Leu Ile Cys Ala Leu Phe Leu Ala Ala Ser Tyr Val Ala
 1               5                  10                  15

Ala Ser Ala Glu Ala Glu Val Lys Val Glu Glu Gly Val Leu Val Ala
                20                  25                  30

Thr Val Asp Asn Phe Lys Gln Leu Ile Ala Asp Asn Glu Phe Val Leu
            35                  40                  45

Val Glu Phe Tyr Ala Pro Trp Cys Gly His Cys Lys Ala Leu Ala Pro
        50                  55                  60

Glu Tyr Ala Lys Ala Ala Gln Gln Leu Ala Glu Lys Glu Ser Pro Ile
65                  70                  75                  80

Lys Leu Ala Lys Val Asp Ala Thr Val Glu Gly Leu Ala Glu Gln
                85                  90                  95

Tyr Ala Val Arg Gly Tyr Pro Thr Leu Lys Phe Phe Arg Ser Gly Ser
                100                 105                 110

Pro Val Glu Tyr Ser Gly Gly Arg Gln Ala Ala Asp Ile Ile Ala Trp
            115                 120                 125

Val Thr Lys Lys Thr Gly Pro Pro Ala Lys Asp Leu Thr Ser Val Ala
130                 135                 140

Asp Ala Glu Gln Phe Leu Lys Asp Asn Glu Ile Ala Ile Ile Gly Phe
145                 150                 155                 160

Phe Lys Asp Leu Glu Ser Glu Ala Lys Thr Phe Thr Lys Val Ala
                165                 170                 175

Asn Ala Leu Asp Ser Phe Val Phe Gly Val Ser Ser Asn Ala Asp Val
            180                 185                 190

Ile Ala Lys Tyr Glu Ala Lys Asp Asn Gly Val Val Leu Phe Lys Pro
        195                 200                 205
```

```
Phe Asp Asp Lys Lys Ser Val Phe Glu Gly Glu Leu Asn Glu Glu Asn
    210                 215                 220

Leu Lys Lys Phe Ala Gln Val Gln Ser Leu Pro Leu Ile Val Asp Phe
225                 230                 235                 240

Asn His Glu Ser Ala Ser Lys Ile Phe Gly Ser Ile Lys Ser His
                245                 250                 255

Leu Leu Phe Phe Val Ser Arg Glu Gly Gly His Ile Glu Lys Tyr Val
                260                 265                 270

Asp Pro Leu Lys Glu Ile Ala Lys Lys Tyr Arg Asp Asp Ile Leu Phe
                275                 280                 285

Val Thr Ile Ser Ser Asp Glu Asp His Thr Arg Ile Phe Glu Phe
    290                 295                 300

Phe Gly Met Asn Lys Glu Glu Val Pro Thr Ile Arg Leu Ile Lys Leu
305                 310                 315                 320

Glu Glu Asp Met Ala Lys Tyr Lys Pro Glu Ser Asp Asp Leu Ser Ala
                325                 330                 335

Glu Thr Ile Glu Ala Phe Leu Lys Lys Phe Leu Asp Gly Lys Leu Lys
                340                 345                 350

Gln His Leu Leu Ser Gln Glu Leu Pro Glu Asp Trp Asp Lys Asn Pro
                355                 360                 365

Val Lys Val Leu Val Ser Ser Asn Phe Glu Ser Val Ala Leu Asp Lys
    370                 375                 380

Ser Lys Ser Val Leu Val Glu Phe Tyr Ala Pro Trp Cys Gly His Cys
385                 390                 395                 400

Lys Gln Leu Ala Pro Ile Tyr Asp Gln Leu Ala Glu Lys Tyr Lys Asp
                405                 410                 415

Asn Glu Asp Ile Val Ile Ala Lys Met Asp Ser Thr Ala Asn Glu Leu
                420                 425                 430

Glu Ser Ile Lys Ile Ser Ser Phe Pro Thr Ile Lys Tyr Phe Arg Lys
                435                 440                 445

Glu Asp Asn Lys Val Ile Asp Phe Asn Leu Asp Arg Thr Leu Asp Asp
                450                 455                 460

Phe Val Lys Phe Leu Asp Ala Asn Gly Glu Val Ala Asp Ser Glu Pro
465                 470                 475                 480

Val Glu Glu Thr Glu Glu Glu Glu Ala Pro Lys Lys Asp Glu Leu
                485                 490                 495

<210> SEQ ID NO 28
<211> LENGTH: 515
<212> TYPE: PRT
<213> ORGANISM: Gallus gallus

<400> SEQUENCE: 28

Met Ala Val Val Arg Val Arg Ala Ile Val Ala Leu Leu Cys Leu Val
  1               5                  10                  15

Ala Ala Leu Gly Leu Ala Glu Pro Leu Glu Glu Glu Asp Gly Val Leu
                20                  25                  30

Val Leu Arg Ala Ala Asn Phe Glu Gln Ala Leu Ala Ala His Arg His
            35                  40                  45

Leu Leu Val Glu Phe Tyr Ala Pro Trp Cys Gly His Cys Lys Ala Leu
        50                  55                  60

Ala Pro Glu Tyr Ala Lys Ala Ala Gln Leu Lys Ala Glu Gly Ser
65                  70                  75                  80

Glu Ile Arg Leu Ala Lys Val Asp Ala Thr Glu Glu Ala Glu Leu Ala
```

-continued

```
                85                  90                  95
Gln Gln Phe Gly Val Arg Gly Tyr Pro Thr Ile Lys Phe Phe Arg Asn
            100                 105                 110
Gly Asp Lys Ala Ala Pro Arg Glu Tyr Thr Ala Gly Arg Glu Ala Asp
            115                 120                 125
Asp Ile Val Ser Trp Leu Lys Lys Arg Thr Gly Pro Ala Ala Thr Thr
130                 135                 140
Leu Thr Asp Ala Ala Ala Glu Thr Leu Val Asp Ser Ser Glu Val
145                 150                 155                 160
Val Val Ile Gly Phe Lys Asp Val Thr Ser Asp Ala Ala Lys Glu
            165                 170                 175
Phe Leu Leu Ala Ala Glu Ser Val Asp Asp Ile Pro Phe Gly Ile Ser
            180                 185                 190
Ser Ser Ala Asp Val Phe Ser Lys Tyr Gln Leu Ser Gln Asp Gly Val
            195                 200                 205
Val Leu Phe Lys Lys Phe Asp Glu Gly Arg Asn Asn Phe Glu Gly Asp
            210                 215                 220
Leu Thr Lys Asp Asn Leu Leu Asn Phe Ile Lys Ser Asn Gln Leu Pro
225                 230                 235                 240
Leu Val Ile Glu Phe Thr Glu Gln Thr Ala Pro Lys Ile Phe Gly Gly
            245                 250                 255
Glu Ile Lys Thr His Ile Leu Leu Phe Leu Pro Lys Ser Val Ser Asp
            260                 265                 270
Tyr Glu Gly Lys Leu Asp Asn Phe Lys Thr Ala Ala Gly Asn Phe Lys
            275                 280                 285
Gly Lys Ile Leu Phe Ile Phe Ile Asp Ser Asp His Ser Asp Asn Gln
            290                 295                 300
Arg Ile Leu Glu Phe Phe Gly Leu Lys Lys Glu Glu Cys Pro Ala Val
305                 310                 315                 320
Arg Leu Ile Thr Leu Glu Glu Met Thr Lys Tyr Lys Pro Glu Ser
            325                 330                 335
Asp Asp Leu Thr Ala Asp Lys Ile Lys Glu Phe Cys Asn Lys Phe Leu
            340                 345                 350
Glu Gly Lys Ile Lys Pro His Leu Met Ser Gln Asp Leu Pro Glu Asp
            355                 360                 365
Trp Asp Lys Gln Pro Val Lys Val Leu Val Gly Lys Asn Phe Glu Glu
            370                 375                 380
Val Ala Phe Asp Glu Asn Lys Asn Val Phe Val Glu Phe Tyr Ala Pro
385                 390                 395                 400
Trp Cys Gly His Cys Lys Gln Leu Ala Pro Ile Trp Asp Lys Leu Gly
            405                 410                 415
Glu Thr Tyr Arg Asp His Glu Asn Ile Val Ile Ala Lys Met Asp Ser
            420                 425                 430
Thr Ala Asn Glu Val Glu Ala Val Lys Ile His Ser Phe Pro Thr Leu
            435                 440                 445
Lys Phe Phe Pro Ala Gly Ser Gly Arg Asn Val Ile Asp Tyr Asn Gly
            450                 455                 460
Glu Arg Thr Leu Glu Gly Phe Lys Lys Phe Leu Glu Ser Gly Gly Gln
465                 470                 475                 480
Asp Gly Ala Ala Ala Asp Asp Leu Glu Asp Leu Glu Thr Asp Glu
            485                 490                 495
Glu Thr Asp Leu Glu Glu Gly Asp Asp Glu Gln Lys Ile Gln Lys
            500                 505                 510
```

Asp Glu Leu
        515

<210> SEQ ID NO 29
<211> LENGTH: 489
<212> TYPE: PRT
<213> ORGANISM: Drosophila melanogaster

<400> SEQUENCE: 29

Met Met Trp Arg Leu Ala Gly Val Leu Leu Gly Phe Ile Ala Ile
 1               5                  10                  15

Ser Ser Gly Ala Asp Glu Asp Val Leu Glu Leu Gly Asp Asp Phe
                20                  25                  30

Ala Thr Thr Leu Lys Gln His Glu Thr Thr Leu Val Met Phe Tyr Ala
            35                  40                  45

Pro Trp Cys Gly His Cys Lys Arg Leu Lys Pro Glu Tyr Ala Lys Ala
        50                  55                  60

Ala Glu Ile Val Lys Asp Asp Pro Pro Ile Lys Leu Ala Lys Val
65                  70                  75                  80

Asp Cys Thr Glu Ala Gly Lys Glu Thr Cys Ser Lys Tyr Ser Val Ser
                85                  90                  95

Gly Tyr Pro Thr Leu Lys Ile Phe Arg Gln Asp Glu Val Ser Gln Asp
                100                 105                 110

Tyr Asn Gly Pro Arg Asp Ser Ser Gly Ile Ala Lys Tyr Met Arg Ala
            115                 120                 125

Gln Val Gly Pro Ala Ser Lys Thr Val Arg Thr Val Ala Glu Leu Lys
        130                 135                 140

Lys Phe Leu Asp Thr Lys Asp Thr Thr Leu Phe Gly Tyr Phe Ser Asp
145                 150                 155                 160

Ser Asp Ser Lys Leu Ala Lys Ile Phe Leu Lys Phe Ala Asp Lys Asn
                165                 170                 175

Arg Glu Lys Tyr Arg Phe Gly His Ser Ser Glu Lys Glu Val Leu Asp
            180                 185                 190

Lys Gln Gly Glu Thr Asp Lys Ile Val Leu Ile Arg Ala Pro His Leu
        195                 200                 205

Ser Asn Lys Phe Glu Ser Ser Ile Lys Phe Glu Gly Ser Ser Glu
    210                 215                 220

Ser Asp Leu Ser Thr Phe Val Lys Glu Asn Phe His Gly Leu Val Gly
225                 230                 235                 240

His Arg Thr Gln Asp Ser Val Lys Asp Phe Gln Asn Pro Leu Ile Thr
                245                 250                 255

Ala Tyr Tyr Ser Val Asp Tyr Gln Lys Asn Pro Lys Gly Thr Asn Tyr
            260                 265                 270

Trp Arg Asn Arg Val Leu Lys Val Ala Lys Glu Phe Val Gly Gln Ile
        275                 280                 285

Asn Phe Ala Ile Ala Ser Lys Asp Asp Phe Gln His Glu Leu Asn Glu
    290                 295                 300

Tyr Gly Tyr Asp Phe Val Gly Asp Lys Pro Val Val Leu Ala Arg Asp
305                 310                 315                 320

Glu Lys Asn Leu Lys Tyr Ala Leu Lys Asp Glu Phe Ser Val Glu Asn
                325                 330                 335

Leu Gln Asp Phe Val Glu Lys Leu Leu Ala Asn Glu Leu Glu Pro Tyr
            340                 345                 350

Ile Lys Ser Glu Pro Ile Pro Glu Ser Asn Asp Ala Pro Val Lys Val

-continued

```
              355                 360                 365
Ala Val Ala Lys Asn Phe Asp Asp Leu Val Ile Asn Asn Gly Lys Asp
        370                 375                 380

Thr Leu Ile Glu Phe Tyr Ala Pro Trp Cys Gly His Cys Lys Lys Leu
385                 390                 395                 400

Thr Pro Ile Tyr Glu Glu Leu Ala Gln Lys Leu Gln Asp Glu Asp Val
                405                 410                 415

Ala Ile Val Lys Met Asp Ala Thr Ala Asn Asp Val Pro Pro Glu Phe
            420                 425                 430

Asn Val Arg Gly Phe Pro Thr Leu Phe Trp Leu Pro Lys Asp Ala Lys
        435                 440                 445

Asn Lys Pro Val Ser Tyr Asn Gly Gly Arg Glu Val Asp Asp Phe Leu
    450                 455                 460

Lys Tyr Ile Ala Lys Glu Ala Thr Thr Glu Leu Lys Gly Phe Asp Arg
465                 470                 475                 480

Ser Gly Lys Pro Lys Lys Thr Glu Leu
                485
```

<210> SEQ ID NO 30
<211> LENGTH: 508
<212> TYPE: PRT
<213> ORGANISM: Homo sapiens

<400> SEQUENCE: 30

```
Met Leu Arg Arg Ala Leu Leu Cys Leu Ala Val Ala Ala Leu Val Arg
  1               5                  10                  15

Ala Asp Ala Pro Glu Glu Glu Asp His Val Leu Val Leu Arg Lys Ser
            20                  25                  30

Asn Phe Ala Glu Ala Leu Ala Ala His Lys Tyr Leu Leu Val Glu Phe
        35                  40                  45

Tyr Ala Pro Trp Cys Gly His Cys Lys Ala Leu Ala Pro Glu Tyr Ala
    50                  55                  60

Lys Ala Ala Gly Lys Leu Lys Ala Glu Gly Ser Glu Ile Arg Leu Ala
65                  70                  75                  80

Lys Val Asp Ala Thr Glu Glu Ser Asp Leu Ala Gln Gln Tyr Gly Val
                85                  90                  95

Arg Gly Tyr Pro Thr Ile Lys Phe Phe Arg Asn Gly Asp Thr Ala Ser
            100                 105                 110

Pro Lys Glu Tyr Thr Ala Gly Arg Glu Ala Asp Asp Ile Val Asn Trp
        115                 120                 125

Leu Lys Lys Arg Thr Gly Pro Ala Ala Thr Thr Leu Pro Asp Gly Ala
    130                 135                 140

Ala Ala Glu Ser Leu Val Glu Ser Ser Glu Val Ala Val Ile Gly Phe
145                 150                 155                 160

Phe Lys Asp Val Glu Ser Asp Ser Ala Lys Gln Phe Leu Gln Ala Ala
                165                 170                 175

Glu Ala Ile Asp Asp Ile Pro Phe Gly Ile Thr Ser Asn Ser Asp Val
            180                 185                 190

Phe Ser Lys Tyr Gln Leu Asp Lys Asp Gly Val Val Leu Phe Lys Lys
        195                 200                 205

Phe Asp Glu Gly Arg Asn Asn Phe Glu Gly Glu Val Thr Lys Glu Asn
    210                 215                 220

Leu Leu Asp Phe Ile Lys His Asn Gln Leu Pro Leu Val Ile Glu Phe
225                 230                 235                 240
```

```
Thr Glu Gln Thr Ala Pro Lys Ile Phe Gly Glu Ile Lys Thr His
                245                 250                 255

Ile Leu Leu Phe Leu Pro Lys Ser Val Ser Asp Tyr Asp Gly Lys Leu
            260                 265                 270

Ser Asn Phe Lys Thr Ala Ala Glu Ser Phe Lys Gly Lys Ile Leu Phe
        275                 280                 285

Ile Phe Ile Asp Ser Asp His Thr Asp Asn Gln Arg Ile Leu Glu Phe
    290                 295                 300

Phe Gly Leu Lys Lys Glu Glu Cys Pro Ala Val Arg Leu Ile Thr Leu
305                 310                 315                 320

Glu Glu Glu Met Thr Lys Tyr Lys Pro Glu Ser Glu Leu Thr Ala
                325                 330                 335

Glu Arg Ile Thr Glu Phe Cys His Arg Phe Leu Glu Gly Lys Ile Lys
            340                 345                 350

Pro His Leu Met Ser Gln Glu Leu Pro Glu Asp Trp Asp Lys Gln Pro
        355                 360                 365

Val Lys Val Leu Val Gly Lys Asn Phe Glu Asp Val Ala Phe Asp Glu
    370                 375                 380

Lys Lys Asn Val Phe Val Glu Phe Tyr Ala Pro Trp Cys Gly His Cys
385                 390                 395                 400

Lys Gln Leu Ala Pro Ile Trp Asp Lys Leu Gly Glu Thr Tyr Lys Asp
                405                 410                 415

His Glu Asn Ile Val Ile Ala Lys Met Asp Ser Thr Ala Asn Glu Val
            420                 425                 430

Glu Ala Val Lys Val His Ser Phe Pro Thr Leu Lys Phe Phe Pro Ala
        435                 440                 445

Ser Ala Asp Arg Thr Val Ile Asp Tyr Asn Gly Glu Arg Thr Leu Asp
    450                 455                 460

Gly Phe Lys Lys Phe Leu Glu Ser Gly Gly Gln Asp Gly Ala Gly Asp
465                 470                 475                 480

Asp Asp Asp Leu Glu Asp Leu Glu Glu Ala Glu Glu Pro Asp Met Glu
                485                 490                 495

Glu Asp Asp Asp Gln Lys Ala Val Lys Asp Glu Leu
                500                 505

<210> SEQ ID NO 31
<211> LENGTH: 364
<212> TYPE: PRT
<213> ORGANISM: Medicago sativa

<400> SEQUENCE: 31

Met Lys Met Glu Met His Gln Ile Trp Ser Arg Ile Ala Leu Ala Ser
 1               5                  10                  15

Phe Ala Phe Ala Ile Leu Phe Val Ser Val Ser Ala Asp Asp Val Val
                20                  25                  30

Val Leu Thr Glu Glu Asn Phe Glu Lys Glu Val Gly His Asp Lys Gly
            35                  40                  45

Ala Leu Val Glu Phe Tyr Ala Pro Trp Cys Gly His Cys Lys Lys Leu
        50                  55                  60

Ala Pro Glu Tyr Glu Lys Leu Pro Asn Ser Phe Lys Lys Ala Lys Ser
65                  70                  75                  80

Val Leu Ile Ala Lys Val Asp Cys Asp Glu His Lys Ser Val Cys Ser
                85                  90                  95

Lys Tyr Gly Val Ser Gly Tyr Pro Thr Ile Gln Trp Phe Pro Lys Gly
            100                 105                 110
```

```
Ser Leu Glu Pro Lys Lys Phe Glu Gly Pro Arg Thr Ala Glu Ser Leu
            115                 120                 125

Ala Glu Phe Val Asn Thr Glu Gly Gly Thr Asn Val Lys Ile Ala Thr
        130                 135                 140

Ala Pro Ser His Val Val Leu Thr Pro Glu Thr Phe Asn Glu Val
145                 150                 155                 160

Val Leu Asp Gly Thr Lys Asp Val Leu Val Glu Phe Tyr Ala Pro Trp
                165                 170                 175

Cys Gly His Cys Lys Ser Leu Ala Pro Ile Tyr Glu Lys Val Ala Ala
            180                 185                 190

Val Phe Lys Ser Glu Asp Val Val Ile Ala Asn Leu Asp Ala Asp
        195                 200                 205

Lys Tyr Arg Asp Leu Ala Glu Lys Tyr Asp Val Ser Gly Phe Pro Thr
210                 215                 220

Leu Lys Phe Phe Pro Lys Gly Asn Lys Ala Gly Glu Asp Tyr Gly Gly
225                 230                 235                 240

Gly Arg Asp Leu Asp Asp Phe Val Ala Phe Ile Asn Glu Lys Ser Gly
                245                 250                 255

Thr Ser Arg Asp Ala Lys Gly Gln Leu Thr Ser Glu Ala Gly Ile Val
            260                 265                 270

Glu Asp Leu Asp Glu Leu Val Lys Glu Phe Val Ala Ala Asn Asp Glu
        275                 280                 285

Glu Lys Lys Ala Val Phe Ala Arg Ile Glu Glu Val Lys Lys Leu
    290                 295                 300

Glu Gly Ser Ala Ser Arg Tyr Gly Lys Ile Tyr Leu Lys Val Ser Lys
305                 310                 315                 320

Lys Tyr Leu Glu Lys Gly Ser Asp Tyr Ala Lys Asn Glu Ile Gln Arg
                325                 330                 335

Leu Glu Arg Leu Leu Glu Lys Ser Ile Ser Pro Ala Lys Ala Asp Glu
            340                 345                 350

Leu Thr Leu Lys Lys Asn Ile Leu Ser Thr Tyr Ala
        355                 360

<210> SEQ ID NO 32
<211> LENGTH: 433
<212> TYPE: PRT
<213> ORGANISM: Drosophila melanogaster

<400> SEQUENCE: 32

Met Arg Gln Leu Ala Ser Ile Leu Leu Leu Ala Phe Val Val Gly Ser
1               5                   10                  15

Val Ser Ala Phe Tyr Ser Pro Ser Asp Gly Val Val Glu Leu Thr Pro
            20                  25                  30

Ser Asn Phe Asp Arg Glu Val Leu Lys Asp Asp Ala Ile Trp Val Val
        35                  40                  45

Glu Phe Tyr Ala Pro Trp Cys Gly His Cys Gln Ser Leu Val Pro Glu
    50                  55                  60

Tyr Lys Lys Leu Ala Lys Ala Leu Lys Gly Val Val Lys Val Gly Ser
65                  70                  75                  80

Val Asn Ala Asp Ala Asp Ser Thr Leu Ser Gly Gln Phe Gly Val Arg
                85                  90                  95

Gly Phe Pro Thr Ile Lys Ile Phe Gly Ala Asn Lys Lys Ser Pro Thr
            100                 105                 110

Asp Tyr Asn Gly Gln Arg Thr Ala Lys Ala Ile Ala Glu Ala Ala Leu
```

-continued

```
                115                 120                 125
Ala Glu Val Lys Lys Val Gln Val Leu Gly Gly Gly Gly
    130                 135                 140
Ser Ser Ser Gly Gly Ser Gly Ser Ser Gly Asp Val Ile Glu
145                 150                 155                 160
Leu Thr Glu Asp Asn Phe Asp Lys Leu Val Leu Asn Ser Asp Asp Ile
                165                 170                 175
Trp Leu Val Glu Phe Phe Ala Pro Trp Cys Gly His Cys Lys Asn Leu
                180                 185                 190
Ala Pro Glu Trp Ala Lys Ala Ala Lys Glu Leu Lys Gly Lys Val Lys
                195                 200                 205
Leu Gly Ala Leu Asp Ala Thr Ala His Gln Ser Lys Ala Ala Glu Tyr
    210                 215                 220
Asn Val Arg Gly Tyr Pro Thr Ile Lys Phe Phe Pro Ala Gly Ser Lys
225                 230                 235                 240
Arg Ala Ser Asp Ala Gln Glu Tyr Asp Gly Gly Arg Thr Ala Ser Asp
                245                 250                 255
Ile Val Ser Trp Ala Ser Asp Lys His Val Ala Asn Val Pro Ala Pro
                260                 265                 270
Glu Leu Ile Glu Ile Ile Asn Glu Ser Thr Phe Glu Thr Ala Cys Glu
                275                 280                 285
Gly Lys Pro Leu Cys Val Val Ser Val Leu Pro His Ile Leu Asp Cys
    290                 295                 300
Asp Ala Lys Cys Arg Asn Lys Phe Leu Asp Thr Leu Arg Thr Leu Gly
305                 310                 315                 320
Glu Lys Phe Lys Gln Lys Gln Trp Gly Trp Ala Trp Ala Glu Gly Gly
                325                 330                 335
Gln Gln Leu Ala Leu Glu Glu Ser Leu Glu Val Gly Gly Phe Gly Tyr
                340                 345                 350
Pro Ala Met Ala Val Val Asn Phe Lys Lys Met Lys Phe Ser Val Leu
                355                 360                 365
Lys Gly Ser Phe Ser Lys Asp Gly Ile Asn Glu Phe Leu Arg Asp Ile
    370                 375                 380
Ser Tyr Gly Arg Gly His Thr Ala Pro Val Arg Gly Ala Lys Lys Pro
385                 390                 395                 400
Ala Ile Val Ser Val Asp Pro Trp Asp Gly Lys Asp Gly Gln Leu Pro
                405                 410                 415
Thr Glu Glu Asp Ile Asp Leu Ser Asp Ile Asp Leu Asp Lys Asp Glu
                420                 425                 430
Leu
```